(12) United States Patent
Stoll et al.

(10) Patent No.: US 11,933,731 B1
(45) Date of Patent: Mar. 19, 2024

(54) SYSTEMS AND METHODS USING SURFACE-ENHANCED RAMAN SPECTROSCOPY FOR DETECTING TETRAHYDROCANNABINOL

(71) Applicant: Hound Labs, Inc., Oakland, CA (US)

(72) Inventors: Jeffrey A. Stoll, San Mateo, CA (US); Samartha G. Anekal, Fremont, CA (US); Karan Mohan, Newark, CA (US)

(73) Assignee: Hound Labs, Inc., Oakland, CA (US)

( * ) Notice: Subject to any disclaimer, the term of this patent is extended or adjusted under 35 U.S.C. 154(b) by 0 days.

(21) Appl. No.: 17/302,801

(22) Filed: May 12, 2021

Related U.S. Application Data

(60) Provisional application No. 63/024,423, filed on May 13, 2020.

(51) Int. Cl.
*G01N 21/65* (2006.01)
*G01N 33/497* (2006.01)

(52) U.S. Cl.
CPC ......... *G01N 21/658* (2013.01); *G01N 33/497* (2013.01); *G01N 2033/4975* (2013.01)

(58) Field of Classification Search
CPC . G01N 33/497; G01N 33/4972; G01N 21/658
See application file for complete search history.

(56) References Cited

U.S. PATENT DOCUMENTS

| | | | |
|---|---|---|---|
| 3,086,833 A | 4/1963 | Streck | |
| 3,393,108 A | 7/1968 | Jones | |
| 3,676,072 A | 7/1972 | Krivis | |
| 4,133,202 A | 1/1979 | Marple | |
| 4,232,667 A | 11/1980 | Chalon et al. | |
| 4,288,344 A | 9/1981 | Reiss | |
| 4,771,005 A | 9/1988 | Spiro | |
| 4,796,475 A | 1/1989 | Marple | |
| 4,926,679 A | 5/1990 | Dewhurst | |
| 5,026,027 A | 6/1991 | Hamilton | |
| 5,103,857 A | 4/1992 | Kuhn et al. | |
| 5,140,993 A | 8/1992 | Opekun, Jr. et al. | |
| 5,196,306 A | 3/1993 | Bobrow et al. | |
| 5,230,866 A | 7/1993 | Shartle et al. | |
| 5,361,771 A | 11/1994 | Craine et al. | |
| 5,438,980 A | 8/1995 | Phillips | |

(Continued)

FOREIGN PATENT DOCUMENTS

| | | | | |
|---|---|---|---|---|
| EP | 0132313 B1 | 9/1991 | | |
| EP | 2498093 A1 * | 9/2012 | ........... | G01N 21/658 |

(Continued)

OTHER PUBLICATIONS

Sean I. Hwang, "Tetrahydrocannabinol Detection Using Semiconductor-Enriched Single-Walled Carbon Nanotube Chemiresistors", 2019 hereafter Hwang (Year: 2019).*

(Continued)

*Primary Examiner* — Maurice C Smith
(74) *Attorney, Agent, or Firm* — Mahamedi IP Law LLP

(57) ABSTRACT

The present disclosure relates to using Surface-Enhanced Raman Spectroscopy (SERS) for detecting analytes in samples. Uses can include, for example, detection of tetrahydrocannabinol (THC) using SERS, as well as apparatuses and systems to implement such detection methods.

21 Claims, 12 Drawing Sheets

(56) References Cited

U.S. PATENT DOCUMENTS

| | | | |
|---|---|---|---|
| 5,583,001 A | 12/1996 | Bobrow et al. | |
| 5,589,346 A | 12/1996 | Kanan et al. | |
| 5,731,158 A | 3/1998 | Bobrow et al. | |
| 5,922,610 A | 7/1999 | Alving et al. | |
| 6,040,191 A * | 3/2000 | Grow | G01N 35/00009 436/172 |
| 6,067,983 A | 5/2000 | Stenzler | |
| 6,326,159 B1 | 12/2001 | Ullman et al. | |
| 6,460,539 B1 | 10/2002 | Japuntich et al. | |
| 6,537,823 B1 | 3/2003 | Smith | |
| 6,582,376 B2 | 6/2003 | Baghdassarian | |
| 6,605,444 B1 | 8/2003 | Klein et al. | |
| 6,727,067 B2 | 4/2004 | Russman et al. | |
| 6,780,617 B2 | 8/2004 | Chen | |
| 6,964,862 B2 | 11/2005 | Chen | |
| 7,059,349 B2 | 6/2006 | Breda | |
| 7,337,072 B2 | 2/2008 | Chen | |
| 7,364,553 B2 | 4/2008 | Paz et al. | |
| 7,547,285 B2 | 6/2009 | Kline | |
| 7,718,421 B2 | 5/2010 | Chen et al. | |
| 7,799,521 B2 | 9/2010 | Chen | |
| 7,833,489 B2 | 11/2010 | Chen | |
| 7,935,504 B2 | 5/2011 | Chen | |
| 8,148,116 B2 | 4/2012 | Chen | |
| 8,237,118 B2 | 8/2012 | Prox et al. | |
| 8,586,932 B2 | 11/2013 | Rousso et al. | |
| 8,705,029 B2 | 4/2014 | Palmskog et al. | |
| 8,707,758 B2 | 4/2014 | Keays | |
| 8,936,933 B2 | 1/2015 | Chen et al. | |
| 8,955,366 B2 | 2/2015 | Abraham-Fuchs et al. | |
| 9,239,323 B2 | 1/2016 | Keays | |
| 9,429,564 B2 | 8/2016 | Beck | |
| 9,617,582 B2 | 4/2017 | Milton et al. | |
| 9,662,652 B2 | 5/2017 | Chen | |
| 9,708,599 B2 | 7/2017 | Chen et al. | |
| 9,709,581 B1 | 7/2017 | Gordon et al. | |
| 9,709,582 B1 | 7/2017 | Gordon et al. | |
| 9,726,684 B1 | 8/2017 | Gordon et al. | |
| 9,921,234 B1 | 3/2018 | Lynn et al. | |
| 9,933,445 B1 | 4/2018 | Lynn et al. | |
| 9,945,878 B1 | 4/2018 | Gordon et al. | |
| 9,970,950 B1 | 5/2018 | Lynn et al. | |
| 9,976,944 B2 | 5/2018 | Olin et al. | |
| 10,226,201 B2 | 3/2019 | Ahmad et al. | |
| 10,247,742 B1 | 4/2019 | Lynn et al. | |
| 10,408,850 B1 | 9/2019 | Gordon et al. | |
| 10,443,050 B2 | 10/2019 | Chen et al. | |
| 10,557,563 B2 | 2/2020 | Thurau | |
| 10,641,783 B2 | 5/2020 | Lynn et al. | |
| 10,955,428 B2 | 3/2021 | Lynn et al. | |
| 11,026,596 B1 | 6/2021 | Lynn et al. | |
| 11,187,711 B1 | 11/2021 | Lynn et al. | |
| 11,426,097 B1 | 8/2022 | Lynn et al. | |
| 2002/0177232 A1 | 11/2002 | Melker et al. | |
| 2003/0153844 A1 | 8/2003 | Smith et al. | |
| 2003/0190259 A1 | 10/2003 | Alley | |
| 2004/0043479 A1 | 3/2004 | Briscoe et al. | |
| 2005/0105077 A1 | 5/2005 | Padmanabhan et al. | |
| 2005/0137491 A1 | 6/2005 | Paz et al. | |
| 2005/0279181 A1 | 12/2005 | Trakumas et al. | |
| 2006/0094123 A1 | 5/2006 | Day et al. | |
| 2006/0195040 A1 | 8/2006 | Nason et al. | |
| 2006/0257941 A1 | 11/2006 | McDevitt et al. | |
| 2007/0031283 A1 | 2/2007 | Davis et al. | |
| 2007/0077660 A1 | 4/2007 | Glas | |
| 2008/0004542 A1 | 1/2008 | Allen et al. | |
| 2008/0038154 A1 | 2/2008 | Longbottom et al. | |
| 2008/0045825 A1 | 2/2008 | Melker et al. | |
| 2008/0050839 A1 | 2/2008 | Suslick et al. | |
| 2009/0017555 A1 | 1/2009 | Jehanli et al. | |
| 2010/0297635 A1 | 11/2010 | Olin et al. | |
| 2011/0086364 A1 | 4/2011 | Takkinen et al. | |
| 2011/0167932 A1 | 7/2011 | Thornburg et al. | |
| 2012/0302907 A1 | 11/2012 | Palmskog et al. | |
| 2012/0329142 A1 | 12/2012 | Battrell et al. | |
| 2013/0006068 A1 | 1/2013 | Gemer et al. | |
| 2013/0011859 A1 | 1/2013 | Putnam et al. | |
| 2013/0021153 A1 | 1/2013 | Keays | |
| 2013/0102018 A1 | 4/2013 | Schentag et al. | |
| 2013/0165806 A1 | 6/2013 | Wondka et al. | |
| 2013/0319239 A1 | 12/2013 | Takenaka et al. | |
| 2014/0094391 A1 | 4/2014 | McDevitt et al. | |
| 2014/0120633 A1 | 5/2014 | Gandini et al. | |
| 2014/0276100 A1 | 9/2014 | Satterfield et al. | |
| 2014/0288454 A1 | 9/2014 | Paz et al. | |
| 2014/0296089 A1 | 10/2014 | Holmes et al. | |
| 2014/0311215 A1 | 10/2014 | Keays et al. | |
| 2014/0366609 A1 | 12/2014 | Beck et al. | |
| 2015/0025407 A1 | 1/2015 | Eichler et al. | |
| 2015/0033824 A1 | 2/2015 | Hammarlund et al. | |
| 2015/0065901 A1 | 3/2015 | Bhatnagar et al. | |
| 2015/0265184 A1 | 9/2015 | Wondka et al. | |
| 2015/0305651 A1 | 10/2015 | Attariwala et al. | |
| 2015/0313608 A1 | 11/2015 | Baudenbacher et al. | |
| 2015/0369830 A1 | 12/2015 | Crichlow | |
| 2016/0000358 A1 | 1/2016 | Lundin et al. | |
| 2016/0032798 A1 | 2/2016 | Herman et al. | |
| 2016/0055359 A1 | 2/2016 | Jensen et al. | |
| 2016/0069810 A1 * | 3/2016 | Walavalkar | G01N 33/18 356/301 |
| 2016/0069919 A1 | 3/2016 | Holmes et al. | |
| 2016/0256656 A1 | 9/2016 | Glenn et al. | |
| 2016/0299125 A1 | 10/2016 | Cristoni et al. | |
| 2017/0023546 A1 | 1/2017 | Holmes et al. | |
| 2017/0122851 A1 | 5/2017 | Thatcher et al. | |
| 2017/0128692 A1 | 5/2017 | Christopher et al. | |
| 2017/0184609 A1 | 6/2017 | Milton et al. | |
| 2017/0197213 A1 | 7/2017 | Nielsen et al. | |
| 2017/0303822 A1 | 10/2017 | Allsworth et al. | |
| 2017/0303823 A1 | 10/2017 | Allsworth et al. | |
| 2018/0038798 A1 * | 2/2018 | Zhang | G01N 21/65 |
| 2018/0120278 A1 | 5/2018 | Hoorfar et al. | |
| 2018/0224471 A1 | 8/2018 | Lynn et al. | |
| 2018/0238916 A1 | 8/2018 | Lynn et al. | |
| 2018/0243523 A1 | 8/2018 | Nason et al. | |
| 2018/0306775 A1 | 10/2018 | Beck et al. | |
| 2019/0039069 A1 | 2/2019 | Marshall et al. | |
| 2019/0160460 A1 | 5/2019 | Keatch et al. | |
| 2020/0124625 A1 | 4/2020 | Dunlop et al. | |
| 2020/0147333 A1 | 5/2020 | Stoll et al. | |
| 2020/0182892 A1 | 6/2020 | Lynn et al. | |
| 2020/0245898 A1 | 8/2020 | Heanue et al. | |
| 2020/0245899 A1 | 8/2020 | Heanue et al. | |
| 2020/0278275 A1 | 9/2020 | Turgul et al. | |
| 2020/0300876 A1 | 9/2020 | Lynn et al. | |
| 2020/0397340 A1 | 12/2020 | Dweik | |
| 2021/0330516 A1 | 10/2021 | Letourneau et al. | |

FOREIGN PATENT DOCUMENTS

| | | |
|---|---|---|
| EP | 2762880 A1 | 8/2014 |
| EP | 2781917 A1 | 9/2014 |
| WO | 9014043 A1 | 11/1990 |
| WO | 2006083269 A2 | 8/2006 |
| WO | 2011029889 A1 | 3/2011 |
| WO | 2016065300 A1 | 4/2016 |
| WO | 2018076099 A1 | 5/2018 |
| WO | 2018185164 A1 | 10/2018 |
| WO | 2018211280 A1 | 11/2018 |
| WO | 2019011750 A1 | 1/2019 |

OTHER PUBLICATIONS

Sarah Milliken, "Self-assembled vertically aligned Au nanorod arrays for surface-enhanced Raman scattering (SERS) detection of Cannabinol", Jan. 12, 2018 (Year: 2018).*

Kundan Sivashanmugan, "Trace Detection of Tetrahydrocannabinol in Body Fluid via Surface-Enhanced Raman Scattering and Principal Component Analysis", 2019 (Year: 2019).*

Sezin Yuksel, "Trace detection of tetrahydrocannabinol (THC) with a SERS-based capillary platform prepared by the in situ microwave synthesis of AgNPs", May 24, 2016 (Year: 2016).*

(56) References Cited

OTHER PUBLICATIONS

Massachusetts Probation Service, "Probation's Plan to Strengthen Drug Testing", Apr. 15, 2016 (Year: 2016).*
"Pexa—The importance of early diagnosis", downloaded on Mar. 25, 2019 from http://pexa.se/en/respiratory-research/the-importance-of-early-diagnosis/.
"Pexa—The search for new biomarkers", downloaded on Mar. 25, 2019 from http://pexa.se/en/respiratory-research/the-search-for-new-biomarkers/.
Piao, Wen et al., "Development of azo-based fluorescent probes to detect different levels of hypoxia," Angew. Chem. Int. Ed. 2013, 52, 13028-13032.
Prodromidis, M.I., "Impedimetric immunosensors—A review", Electrochimica Acta, (May 30, 2010), 55(14):4227-33.
Quintela, Oscar et al., "Recovery of drugs of abuse from the immunalysis quantisal oral fluid collection device," Journal of Analytical Toxicology, vol. 30, Oct. 2006.
Rahim S.A. et al., "Colorimetric determination of ethanol in the presence of methanol and other species in aqueous solution," Talanta. Nov. 1992;39(11):1489-91, PubMed abstract 18965558.
Rohrich, J et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.
Russo, E. et al., "A tale of two cannabinoids: the therapeutic rational for combining tetrahydrocannabinol and cannabidiol," Med Hypotheses. 2006;66(2):234-46, PubMed abstract 16209908.
Saalberg, Yannick and Marcus Wolff, "VOC breath biomarkers in lung cancer", Clinica Chimica Acta, (Aug. 1, 2016), 459:5-9.
Samitas, K., et al., "Exhaled cysteinyl-leukotrienes and 8-isoprostane in patients with asthma and their relation to clinical severity", Respiratory medicine, (May 1, 2009), 103(5):750-6.
Samyn N et al., "On-site testing of saliva and sweat with Drugwipe and determination of concentrations of drugs of abuse in saliva, plasma and urine of suspected users," Int J Legal Med. 2000;113(3): 150-4, PubMed abstract 10876986.
Sarafian, Theodor et al., "Inhaled marijuana smoke disrupts mitochondrial energetics in pulmonary epithelial cells in vivo," Am J Physiol Lung Cell Mol Physiol, 2006, 290. L1202-L1209. (Year:2006).
Scheuplein, Robert J., "Mechanism of percutaneous absorption. II. Transient diffusion and the relative importance of various routes of skin penetration," J. Invest. Dermatol 1967;48:79.
Schwartz, Richard H. et al., "Laboratory detection of marijuana use, Experience with a photometric immunoassay to measure urinary cannabinoids," Aj J Dis Child. 1985;139(11): 1093-1096, abstract.
Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).
Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).
Sigma, "How Proximity Ligation Assays (PLA) Work".
Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002;126(1): 17-23, PubMed abstract 11955826.
Soares, J.R et al., "Significant developments in radioimmune methods applied to delta9-THC and its 9-substituted metabolites," Analysis of Cannabinoids Research Monograph 42, NIDA 1982.
"Drug detection, health monitoring etc.", SensAbues AB—Innovation, downloaded on Mar. 25, 2019 from http://sensabues.com/innovation.
"Exhaled breath sampling company", SensAbues AB—About, downloaded on Mar. 25, 2019 from http://sensabues.com/about.
Stevenson H, Bacon A, Joseph KM, Gwandaru WR, Bhide A, Sankhala D, Dhamu VN, Prasad S. "A rapid response electrochemical biosensor for detecting THC in saliva", Scientific reports. Sep. 3, 2019; 9(1): 1-11. (11 pages) // 9:12701 https://doi.org/10.1038/s41598-019-49185-y.
Stiles PL, Dieringer JA, Shah NC, Van Duyne RP. "Surface-enhanced Raman spectroscopy", Annu. Rev. Anal. Chem.. Jul. 19, 2008;1:601-26.
Stinchcomb, A.L. et al., "Human skin permeation of Delta8-tetrahydrocannabinol, cannabidiol and cannbinol," J Pharm Pharmacol. Mar. 2004;56(3):291-7, PubMed abstract 15025853.
Strano-Rossi, Sabina et al., "Analysis of stimulants in oral fluid and urine by gas chromatography-mass spectrometry II: Pseudophedrine," Journal of Analytical Toxicology, vol. 34, May 2010.
Switz, N. A., et al., "Low-Cost Mobile Phone Microscopy with a Reversed Mobile Phone Camera Lens", PloS one, (May 22, 2014), 9(5):e95330. 7 pages.
Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.
Teshima, N et al., "Determination of acetone in breath", Analytica Chimica Acta, 2005, 535, pp. 189-199.
"The Chemistry of Phenols," Zvi Rappoport, editor, @ 2003 John Wiley Sons, Ltd. ISBN: 0-471-49737-1.
Toennes, Stefan W. et al., "Pharmacokinetic properties of delta9-tetrahydrocannabinol in oral fluid of occasional and chronic users," Journal of Analytical Toxicology, vol. 34, May 2010.
Townsend, Doug, Ian Eustis, Mark Lewis, Steven Rodgers, Kevin Smith, Ariel Bohman, C. T. Shelton, and C. A. Sacramento. "The Determination of Total THC and CBD Content in Cannabis Flower by Fourier Transform Near Infrared Spectroscopy." (2018); Document No. 014329_01, 5 pages, accessed at perkinelmer.com/lab-solutions/resources/docs/app_determination_of_thc_and_cbd_cannabisflower.pdf.
Turner, Carton E. et al., "Constituents of cannabis sativa I. XVII. A review of the natural constituents," J. Nat. Prod. 1980;43:169.
Ullman EF, Kirakossian H, Switchenko AC, Ishkanian J, Ericson M, Wartchow CA, Pirio M, Pease J, Irvin BR, Singh S, Singh R. "Luminescent oxygen channeling assay (LOCI): sensitive, broadly applicable homogeneous immunoassay method", Clinical chemistry. Sep. 1, 1996;42(9):1518-26.
Vahimaa P et al., "Surface-Enhanced Raman Spectroscopy (SERS)," Institute of Photonics at the University of Eastern Finland, accessible at sway.com/s/XtgAoh8F5QewSEFL/embed.
Valiveti, S et al., "In vitro/in vivo correlation studies for transdermal delta 8-THC development," J Pharm Sci. May 2004;93(5): 1154-64, PubMed abstract 15067692.
Van der Kooy, F. et al., "Cannabis smoke condensate I: The effect of different preparation methods on tetrahydrocannabinol levels," Inhalation Toxicology, 20:801-804, 2008.
Vinciguerra, V. et al., "Inhalation marijuana as an antiemetic for cancer chemotherapy," NY State J Med. Oct. 1988;88 (10):525-7.
"Volatile Organic Compounds (VOC) as non-invasive biomarkers for a range of diseases", downloaded on Mar. 25, 2019 from https://www.owlstonemedical.com/science-technology/voc-biomarkers/.
Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.
Wall, M.E. et al., "The metabolism of delta 9-tetrahydrocannabinol and related cannabinoids in man," J Clin Pharmacol. Sep.-Aug. 1981;21 (8-9 Suppl): 178S-189S, PubMed abstract 6271823.
Walsh, J. Michael et al., "An evaluation of rapid point-of-collection oral fluid drug-testing devices," Journal of Analytical Toxicology, vol. 27, Oct. 2003.
Wan, G.H., et al., "Cysteinyl leukotriene levels correlate with 8-isoprostane levels in exhaled breath condensates of atopic and healthy children", Pediatric research (Nov. 2013), 74(5):584.
Wang, AX, Kong X. Review of recent progress of plasmonic materials and nano-structures for surface-enhanced Raman scattering. Materials. Jun. 2015;8(6):3024-52.
Watanabe, K. et al., "Brain microsomal oxidation of delta 8- and delta 9- tetrahydrocannabinol," Biochem Biophys Res Commun. Nov. 30, 1988;157(1):75-80, PubMed abstract 2848522.

(56) References Cited

OTHER PUBLICATIONS

Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.

Wiegand, D.M. et al., "Evaluation of police officers exposure to secondhand cannabis smoke at open-air stadium events", NIOSH health hazard evaluation report ; HHE 2017-0174-335, (Mar. 2019), https://www.cdc.gov/niosh/hhe/reports/pdfs/2017-0174-3335.pdf.

Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.

Wingert, William E., "Lowering cutoffs for initial and confirmation testing for cocaine and marijuana: large-scale study of effects on the rates of drug-positive results," Clinical Chemistry 43:1 100-103 (1997).

Written Opinion of the Searching Authority dated Apr. 6, 2020, for International Patent Application No. PCT/US2020/13553, 7 pages.

Emelyanov, A., et al., "Elevated concentrations of exhaled hydrogen peroxide in asthmatic patients", Chest, (Oct. 1, 2001), 120(4): 1136-9.

"SensAbues AB—Next generation drug detection and health monitoring", SensAbues AB—Home, downloaded on Mar. 25, 2019 from http://sensabues.com/home.

"Exhaled breath biological sample matrix. EB", SensAbues AB—Product, downloaded on Mar. 25, 2019 from http://sensabues.com/product.

"FAIMS Breathalyzer Device", downloaded on Mar. 25, 2019 from https://algernonpharmaceuticals.com/faims-breathalyzer-device/.

Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.

Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.

Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3): 147-52, PubMed abstract 15240035.

Fraser, A.D. et al., "Urinary excretion profiles of 11-nor-9-carboxy-Delta9-tetrahydrocannabinol. Study III. A Delta9- THC-COOH to creatinine ratio study," Forensic Sci Int. Nov. 26, 2003;137(2-3): 196-202, PubMed abstract 14609657.

Garrett, Edward R. et al., "Physicochemical properties, solubility, and protein binding of Delta9-tetrahydrocannabinol," J Pharm Sci. Jul. 1974;63(7): 1056-64, abstract.

Garrett, E.R. et al., "Pharmacokinetics of delta9-tetrahydrocannabinol in dogs," J Pharm Sci. Mar. 1977;66(3):395-407, PubMed abstract 845807.

Gjerde, H. et al., "Incidence of alcohol and drugs in fatally injured car drivers in Norway," Accid Anal Prev. Aug. 1993;25(4):479-83, PubMed abstract 8357462.

Gjerde, Hallvard et al., "Comparison of drug concentrations in blood and oral fluid collected with the Intercept® sampling device," Journal of Analytical Toxicology, vol. 34, May 2010.

Goodwin, R.S. et al., "Delta(9)-tetrahydrocannabinol, 11-hydroxy-delta(9)-tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.

Gramse G, Dols-Perez A, Edwards MA, Fumagalli L, Gomila G. Nanoscale measurement of the dielectric constant of supported lipid bilayers in aqueous solutions with electrostatic force microscopy. Biophysical journal. Mar. 19, 2013;104 (6):1257-62.

Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).

Grob NM, Aytekin M, Dweik RA. "Biomarkers in exhaled breath condensate: a review of collection, processing and analysis", Journal of breath research, (Sep. 8, 2008), 2(3):037004.

Gross, Stanley J et al., "Detection of recent cannabis use by saliva Delta9-THC radioimmunoassay," Journal of Analytical Toxicology, vol. 9, Jan./Feb. 1985.

Grotenhermen, F., "Pharmacokinetics and pharmacodynamics of cannabinids," Clin Pharmacokinet. 2003;42 (4):327-60, PubMed abstract 12648025.

Gustafson, R.A et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with positive chemical ionization," J. Chromatogr B Analyt Technol Biomed Life Sci, Dec. 6, 2003;798(1):145-54, PubMed abstract 14630369.

Gustafson, Richard A. et al., "Urinary cannabinoid detection times after controlled oral administration of Delta9-tetrahydrocannabinol to humans," Clinical Chemistry 49:7, 1114-1124 (2003).

Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.

Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.

Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.

Halldin, M.M. et al., "Identification of in vitro metabolites of delta 1-tetrahydrocannabinol formed by human livers," Drug Metab Dispos. Jul.-Aug. 1982 10(4):297-301, PubMed abstract 6126323.

Hampson, A.J. et al., "Cannabidiol and (-)delta9-tetrahydrocannabinol are neuroprotective antioxidants," Proc Natl Acad Sci U.S.A. Jul. 7, 1998; 95(14): 8268-8273.

Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.

Harder, S. et al., "Concentration-effect relationship of delta-9-tetrahydrocannabiol and prediction of psychotropic effects after smoking marijuana," Int J Clin Pharmacol Ther. Apr. 1997;35(4): 155-9, PubMed abstract 9112136.

Harvey, D.J. et al., "Metabolites of cannabidiol identified in human urine," Xenobiotic, Mar. 1990; 20(3):303-20, PubMed abstract 2336840.

Hasan, R.A., et al., "Lipoxin A4 and 8-isoprostane in the exhaled breath condensate of children hospitalized for status asthmaticus", Pediatric critical care medicine: a journal of the Society of Critical Care Medicine and the World Federation of Pediatric Intensive and Critical Care Societies, (Mar. 2012), 13(2):141.

Hawks, Richard L., "The Analysis of Cannabinoids in Biological Fluids," NIDA Research Monograph 42, 1982.

Hazekamp, Arno et al., "Cannabis; extracting the medicine," thesis/dissertation 2007.

Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.

Himes, Sarah K. et al., "Cannabinoids in exhaled breath following controlled administration of smoked cannabis," Clinical chemistry 59:12 1780-1789 (2013).

Huang, Wei et al., "Simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.

(56) References Cited

OTHER PUBLICATIONS

Huestis, M.A. et al., "Characterization of the absorption phase of marijuana smoking," Clin Pharmacol Ther. Jul. 1992;52(1):31-41, PubMed abstract 1320536.
Huestis, Marilyn A. et al., "Alternative testing matrices," chapter 11 of the Drug Abuse Handbook, 1998 CRC Press LLC, ISBN 0-8493-2637-0.
Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.
Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.
Huestis, Marilyn A. et al., "Cannabinoid concentrations in hair from documented cannabis users," Forensic Sci Int. Jul. 4, 2007; 169(2-3): 129-136.
Huestis, Marilyn A. et al., "Detection times of marijuana metabolites in urine by immunoassay and GC-MS," Journal of Analytical Toxicology, vol. 19, Oct. 1995.
Huestis, Marilyn A. et al., "Differentiating new marijuana use from residual drug excretion in occasional marijuana users," Journal of Analytical Toxicology, vol. 22, Oct. 1998.
Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).
Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.
Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.
Huestis, Marilyn A., "Human cannabinoid pharmacokinetics," Chem Biodivers. Aug. 2007; 4(8): 1770-1804.
Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.
Hunt, C.A. et al., "Tolerance and disposition of tetrahydrocannabinol in man," J Pharmacol Exp Ther. Oct. 1980;215(1):35-44, PubMed abstract 6256518.
"Information for health care professionals: cannabis (marihuana, marijuana) and the cannabinoids," Health Canada, Feb. 2013.
International Preliminary Report on Patentability dated Jul. 27, 2021, for International Patent Application No. PCT/US2020/13553, 8 pages.
International Preliminary Report on Patentability dated May 11, 2021, for International Patent Application No. PCT/US2019/060342, 9 pages.
Written Opinion of the Searching Authority dated Jan. 23, 2020, for International Patent Application No. PCT/US2019/060342, 9 pages.
Yang Hu, DArchangel J, Sundheimer ML, Tucker E, Boreman GD, Raschke MB. "Optical dielectric function of silver", Physical Review B. Jun. 22, 2015;91(23):235137.
Zajicek, J et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.
Zanconato, S., et al., "Leukotrienes and 8-isoprostane in exhaled breath condensate of children with stable and unstable asthma", Journal of Allergy and Clinical Immunology, (Feb. 1, 2004), 113(2):257-63.
Zhou, J., "Review of recent developments in determining volatile organic compounds in exhaled breath as biomarkers for lung cancer diagnosis", Analytica chimica acta, (Dec. 15, 2017), 996:1-9.

Zhu, H.J., Wang JS, Markowitz JS, Donovan JL, Gibson BB, Gefroh HA, DeVane CL., "Characterization of P-glycoprotein inhibition by major cannabinoids from marijuana", Journal of Pharmacology and Experimental Therapeutics. May 1, 2006;317(2):850-7.
Zias, Joe et al., "Early medical use of cannabis," Nature; May 20, 1993; 363,6426; Research Library Core p. 215.
Zuardi, A.W. et al., "Action of cannabidiol on the anxiety and other effects produced by delta 9-THC in normal subjects," Psychopharmacology (Berl). 1982;76(3):245-50, PubMed abstract 6285406.
Adams, I.B. et al., "Cannabis: pharmacology and toxicology in animals and humans," Addiction, Nov. 1996;91(11): 1585-614, PubMed abstract 8972919.
Coucke et al., "Tetrahydrocannabinol concentrations in exhaled breath and physiological effects following cannabis intake—A pilot study using illicit cannabis", Clinical Biochemistry, 2016, pp. 1072-1077.
Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.
Alexander, Brentan R., "Design of a microbreather for two-phase microchannel devices", Dissertation submitted to Massachusetts Institute of Technology. Dept. of Mechanical Engineering, (Jun. 2008), 59 pages.
Aliberti, S, et al., "Serum and exhaled breath condensate inflammatory cytokines in community-acquired pneumonia: a prospective cohort study", Pneumonia (Nathan), (Jun. 23, 2016), 8:8. doi: 10.1186/s41479-016-0009-7. eCollection 2016.
Andrews, Travis M., "Breathalyzers of the Future Today," The Atlantic, Jun. 27, 2013. Downloaded from the Internet on Feb. 4, 2019, http://www.theatlantic.com/health/archive/2013/06/breathalyzers-of-the-future-today/277249/.
Atkinson, H.C. et al., "Drugs in human milk. Clinical pharmacokinetic considerations." Clin Pharmacokinet. Apr. 1988; 14(4):217-40, PubMed abstract 3292101.
Azorlosa, J.L. et al., "Marijuana smoking: effect of varying delta 9-tetrahydrocannabinol content and number of puffs," J. Pharmacol. Exper. Ther 1992;261:114, abstract.
Bailey, J.R. et al., "Fetal disposition of delta 9-tetrahydrocannabinol (THC) during late pegnancy in the rhesus monkey," Toxicol Appl Pharmacol. Sep. 15, 1987;90(2):315-21, abstract.
Bajaj, P., and F.T. Ishmael, "Exhaled breath condensates as a source for biomarkers for characterization of inflammatory lung diseases", Journal of Analytical Sciences, Methods and Instrumentation, (Mar. 20, 2013), 3(01):17.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beaudet L, Rodriguez-Suarez R, Venne MH, Caron M, Bedard J, Brechler V, Parent S, Bielefeld-Sevigny M. "AlphaLISA immunoassays: the no-wash alternative to ELISAs for research and drug discovery", Nature Methods, (Dec. 2008), 5(12):an8-9.
Beck, O., et al., "Detection of drugs of abuse in exhaled breath using a device for rapid collection: comparison with plasma, urine and self-reporting in 47 drug users" Journal of breath research, (Apr. 25, 2013), 7(2):026006.
Beck, Olof et al., "Detection of Delta9-tetrahydrocannabinol in exhaled breath collected from cannabis users," Journal of Analytical Toxicology, vol. 35, Oct. 2011.
Benowitz, Neal L. et al., "Metabolic and psychophysiologic studies of cannabidiol-hexobarbital interaction," Clinical Pharmacology and Therapeutics (1980) 28, 115-120, abstract.
Blanc, Jennifer A. et al., "Adsorption losses from urine-based cannabinoid calibrators during routine use," Clin. Chem. 39/8, 1705-1712 (1993).
Bloom, A.S., Effect of delta9-tetrahydrocannabinol on the synthesis of dopamine and norepinephrine in mouse brain synaptosomes, J Pharmacol Exp Ther. Apr. 1982;221(1):97-103.

(56) References Cited

OTHER PUBLICATIONS

Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.

Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.

Brenneisen, R. et al., "The effect of orally and rectally administered delta 9-tetrahydrocannabinol on spaticity: a pilot study with 2 patients," Int J Clin Pharmocol Ther. Oct. 1996;34(10):446-52.

Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.

Burstein, S. et al., "Isolation and characterization of two major urinary metabolites of 1-tetrahydrocannabinol," Science, Apr. 28, 1972;176(4033):422-3, PubMed abstract 5026162.

Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.

Carpenter, C.T., Price PV, Christman BW. Exhaled breath condensate isoprostanes are elevated in patients with acute lung injury or ARDS. Chest. Dec. 1, 1998;114(6):1653-9.

Cecinato, A., Balducci C, Perilli M., "Illicit psychotropic substances in the air: The state-of-art", Sci Total Environ, (Jan. 1, 2016), 539:1-6. doi: 10.1016/j.scitotenv.2015.08.051. Epub Sep. 8, 2015. PMID: 26360454.

Challapalli, P.V. et al., "In vitro experiment optimization for measuring tetrahydrocannabinol skin permeation," Int J Pharm. Jul. 25, 2002;241(2):329-39, PubMed abstract 12100860.

Chaturvedi, Arvind K., "Postmortem aviation forensic toxicology: an overview," Journal of Analytical Toxicology, vol. 34, May 2010.

Chiang, C. Nora et al., "Prenatal drug exposure: kinetics and dynamics," NIDA Research Monograph 60, 1985.

Christophersen, Asbjorg Solberg et al., "Tetrahydrocannabinol stability in whole blood: plastic versus glass containers," Journal of Analytical Toxicology, vol. 10, Jul./Aug. 1986.

Chuah K, Wu Y, Vivekchand SR, Gaus K, Reece PJ, Micolich AP, Gooding JJ. "Nanopore blockade sensors for ultrasensitive detection of proteins in complex biological samples", Nature communications, (May 8, 2019), 10(1):1-9. (9 pages).

Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.

Cone, Edward J. et al., "In vivo adulteration: excess fluid ingestion causes false-negative marijuana and cocaine urine test results, " Journal of Analytical Toxicology, vol. 22, Oct. 1998.

Cone, Edward J. et al., "Marijuana-laced brownies: behavioral effects, physiologic effects, and urinalysis in humans following ingestion," Journal of Analytical Toxicology, vol. 12, Jul./Aug. 1988.

Cone, EJ, Johnson RE, Darwin WD, Yousefnejad D, Mell LD, Paul BD, Mitchell J., "Passive inhalation of marijuana smoke: urinalysis and room air levels of delta-9-tetrahydrocannabinol", J Anal Toxicol. (May-Jun 1987), 11(3):89-96. doi: 10.1093/jat/11.3.89. PMID: 3037193.

Crouch, Dennis J. et al., "An evaluation of selected oral fluid point-of-collection drug-testing devices," Journal of Analytical Toxicology, vol. 29, May/Jun. 2005.

Crouch, D.J., "Oral fluid collection: the neglected variable in oral fluid testing," Forensic Sci Int. Jun. 10, 2005;150 (2-3): 165-73, PubMed abstract 15899565.

D'Ambrosio, M. et al., "Point-of-care quantification of blood-borne filarial parasites with a mobile phone microscope", Science Translational Medicine (May 6, 2015), vol. 7, Issue 286, pp. 286re4. 10 pages.

Day, David et al., "Detection of THCA in oral fluid by GC-MS-MS," Journal of Analytical Toxicology, vol. 30, Nov./Dec. 2006.

Doran, GS, Deans R, De Filippis C, Kostakis C, Howitt JA., "Work place drug testing of police officers after THC exposure during large volume cannabis seizures", Forensic Sci Int. (Jun. 2017), 275:224-233. doi: 10.1016/j.forsciint.2017.03.023. Epub Apr. 2, 2017. PMID: 28412574.

D'Souza, Deepak Cyril et al., "The psychotomimetic effects of intravenous delta-9-tetrahydrocannabinol in healthy individuals: implications for psychosis," Neuropsychopharmacology (2004) 29, 1558-1572.

Dunk, et al., "Development of a Portable Marijuana Breathalyzer", (Mar. 2018), URL=http://https://houndlabs.com/wp-content/uploads/2018/03/Hound-TRT-Pittcon-Poster.pdf.

Ellis, George M. Jr. et al. "Excretion patterns of cannabinoid metabilites after last use," 420 Magazine, Oct. 4, 2011, downloaded from https://www.420magazine.com/forums/drug-testing-urine/153724.

Ellis, G.M. Jr. et al., "Excretion patterns of cannabiniod metabolites after last use in a group of chronic users," Clin Pharmacol Ther. Nov. 1985;38(5):572-8, PubMed abstract 3902318.

Elsohly, M. et al., "Potency trends of Delta9-THC and other cannabinoids in confiscated marijuana from 1980-1997," Journal of Forensic Sciences, vol. 45, No. 1, 2000, pp. 24-30.

International Search Report dated Apr. 6, 2020, for International Patent Application No. PCT/US2020/13553, 2 pages.

International Search Report dated Jan. 23, 2020, for International Patent Application No. PCT/US2019/060342, 2 pages.

Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.

Jehanli, A. et al., "Blind trials of an onsite saliva drug test for marijuana and opiates," J Forensic Sci. Sep. 2001;46(5):1214-20, PubMed 11569567.

Joern, William A., "Surface adsorption of the urinary marijuana carboxy metabolite: the problem and a partial solution," Letter to the Editor, Journal of Analytical Toxicology, vol. 16, Nov./Dec. 1992.

Johannson, E. et al., "Terminal elimination plasma half-life of delta 1-tetrahydrocannabinol (delta 1-THC) in heavy users of marijuana," Eur J Clin Pharmacol. 1989;37(3):273-7, PubMed abstract 2558889.

Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.

Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.

Johansson, Eva et al., "Urinary excretion half-life of delta1-tetrahydrocannabinol-7-oic acid in heavy marijuana users after smoking," Journal of Analytical Toxicology, vol. 13, Jul./Aug. 1989.

Jokerst JV, Chen Z, Xu L, Nolley R, Chang E, Mitchell B, Brooks JD, Gambhir SS. A magnetic bead-based sensor for the quantification of multiple prostate cancer biomarkers. PloS ONE. (Sep. 30, 2015), 10(9):e0139484. (15 pages).

Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.

Karst, Matthias et al., "Analgesic effect of the synthetic cannabinoid CT-3 on chronic neuropathic pain," JAMA. 2003;290(13):1757-1762.

Kelly, Peggy et al., "Metabolism of tetrahydrocannabinol in frequent and infrequent marijuana users," Journal of Analytical Toxicology, vol. 16, Jul./Aug. 1992.

Kemp, Philip M. et al., "Cannabinoids in Humans. I. Analysis of delta9-tetrahydrocannabinol and six metabolites in plasma and urine using GC-MS," Journal of Analytical Toxicology, vol. 19, Sep. 1995.

Kemp, Philip M. et al., "Cannabinoids in Humans. II. The influence of three methods of hydrolysis on the concentration of THC and two metabolites in urine," Journal of Analytical Toxicology, vol. 19, Sep. 1995.

(56) References Cited

OTHER PUBLICATIONS

Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.
Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.
Kintz, Pascal et al., "Detection of cannabis in oral fluid (saliva) and forehead wipes (sweat) from impaired drivers," Journal of Analytical Toxicology, vol. 24, Oct. 2000.
Kintz, Pascal et al., "Sweat testing for heroin and metabolites in a heroin maintenance program, " Clinical Chemistry 43:5, 736-739 (1997).
Klejnowski, K et al. "Number Size Distribution of Ambient Particles in a Typical Urban Site: The First Polish Assessment Based on Long-Term (9 Months) Measurements", The Scientific World Journal, (Oct. 2013), 2013 (1):539568.
Kodavanti, U.P. "Respiratory toxicity biomarkers", In Biomarkers in Toxicology, (Jan. 1, 2014) (pp. 217-239). Academic Press.
Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.
Krenke, K. et al., "Inflammatory cytokines in exhaled breath condensate in children with inflammatory bowel diseases", Pediatric pulmonology, (Dec. 2014), 49(12):1190-5.
Kreuz, D.S. et al., "Delta-9-tetrahydrocannabinol: localization in body fat," Science, Jan. 26, 1973;179(4071): 391-3, PubMed abstract 4682965.
Krishna, D.R. et al., "Extrahepatic metabolism of drugs in humans," Clin Pharmacokinet. Feb. 1994;26(2):144-60, PubMed abstract 8162658.
Lafolie, P. et al., "Importance of creatinine analyses of urine when screening for abused drugs," Clin. Chem. 37/11, 1927-1931 (1991).
Laloup, M. et al., "Correlation of delta9-tetrahydrocannabinol concentrations determined by LC-MS-MS in oral fluid and plasma from impaired drivers and evaluation of the on-site Drager Drug Test," Forensic Sci Int. 2006 Srp 12;161 (2-3):175-9, PubMed abstract 16842950.
Law, B. et al., "Forensic aspects of the metabolism and excretion of cannabinoids following oral ingestion of cannabis resin," J Pharm Pharmacol. May 1984;36(5):289-94, PubMed abstract 6145762.
Le Ru EC, Blackie E, Meyer M, Etchegoin PG. Surface enhanced Raman scattering enhancement factors: a comprehensive study. The Journal of Physical Chemistry C. Sep. 20, 2007;111(37): 13794-803.
Lee, Sooyeun et al., "Estimation of the measurement uncertainty by the bottom-up approach for the determination of methamphetamine and amphetamine in urine," Journal of Analytical Toxicology, vol. 34, May 2010.
Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.
Lemberger, L. et al., "Delta-9-tetrahydrocannabinol: metabolism and disposition in long-term marihuana smokers," Science. Jul. 2, 1971;173(3991):72-4, PubMed abstract 5087483.
Lemberger, L. et al., "Marihuana: studies on the disposition and metabolism of delta-9-tetrahydrocannabinol in man," Science. Dec. 18, 1970;170(3964): 1320-2, PubMed abstract 5479011.
Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.
"Low cost, non-invasive and non-intrusive", SensAbues AB—Benefits, downloaded on Mar. 25, 2019 from http://sensabues.com/benefits.

Malfait, A.M. "The nonpsychoactive cannabis constituent cannabidiol is an oral anti-arthritic therapeutic in murine collagen-induced arthritis," Proc Natl Acad Sci USA Aug. 15, 2000;97(17):9561-9566.
Manno, Joseph E. et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.
Manolis, Antony et al., "The detection of delta9-tetrahydrocannabinol in the breath of human subjects," Clinical Biochem. 16,229 (1983).
"Marihuana 84," Proceedings of the Oxford Symposium on Cannabis, D.J. Harvy, editor, IRL Press, Oxford 1984.
Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.
Mason, A.P. et al., "Cannabis: pharmacology and interpretation of effects," J Forensic Sci. Jul. 1985;30(3):615-31, PubMed abstract 2993473.
Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.
Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.
Mattes, R.D. et al., "Bypassing the first-pass effect for the therapeutic use of cannabinoids," Pharmacol Biochem Behav. Mar. 1993;44(3):745-7, PubMed abstract 8383856.
Mattes, R.D. et al., "Cannabinoids and appetite stimulation," Pharmacol Biochem Behav. Sep. 1994;49(1):187-95, PubMed abstract 7816872.
McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.
Mechoulam, Raphael et al., "Cannabidiol: an overview of some chemical and pharmacological aspects. Part I: chemical aspects," Chemistry and Physics of Lipids 121 (2002) 35-43.
Mechoulam, Raphael, "Plant cannabinoids: a neglected pharmacological treasure trove," Br J Pharmacol. Dec. 2005; 146(7): 913-915.
Meier, H. et al., "Cannabis poisoning after eating salad," Schweiz Med Wochenschr. Feb. 8, 1997;127(6):214-8, PubMed abstract 9157527.
Menkes, D.B. et al., "Salivary THC following cannabis smoking correlates with subjective intoxication and heart rate," Psychopharmacology (Berl). 1991;103(2):277-9, PubMed abstract 1851311.
Mikuriya, Tod H., "Cannabis as a substitute for alcohol: a harm-reduction approach," Journal of Cannabis Therapeutics, vol. 4(1) 2004.
Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.
Moeller, M.R. et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.
Moldoveanu, Serban C. et al., "Differences in the chemical composition of the particulate phase of inhaled and exhaled cigarette mainstream smoke," Contributions to Tobacco Research 22(4), 290 (2007).
Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.
Moore, Christine et al., "Application of two-dimensional gas chromatography with electron capture chemical ionization mass spec-

(56) References Cited

OTHER PUBLICATIONS trometry to the detection of 11-nor-delta9-tetrahydrocannabinol-9-carboxylic acid (THC-COOH) in hair," Journal of Analytical Toxicology, vol. 30, Apr. 2006.
Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.
Moore, Christine et al., "The determination of 11-nor-delta9-tetrahydrocannabinol-9-carboxylic acid (THC-COOH) in hair using negative ion gas chromatography-mass spectrometry and high-volume injection," Journal of Analytical Toxicology, vol. 25, Oct. 2001.
Morland, J. et al., "Cannabinoids in blood and urine after passive inhalation of cannabis smoke," J Forensic Sci. Oct. 1985;30(4):997-1002, PubMed abstract 2999292.
Mule, S.J. et al., "Active and realistic passive marijuana exposure tested by three immunoassays and GC/MS in urine," Journal of Analytical Toxicology, vol. 12, May/Jun. 1988.
Mura, P. et al., "Evaluation of six rapid tests for screening of cannabis in sweat, saliva and tears," Acta Clin Belg. 1999;53 Suppl 1:35-8, PubMed abstract 10216980.
Mura, P. et al., "THC can be detected in brain while absent in blood," Letter to the Editor, Journal of Analytical Toxicology, vol. 29, Nov./Dec. 2005.
Nadulski T. et al., "Simultaneous and sensitive analysis of THC, 11-OH-THC, THC-COOH, CBD, and CBN by GC-MS in plasma after oral application of small doses of THC and cannabis extract," Journal of Analytical Toxicology, vol. 29, Nov./Dec. 2005.
Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.
Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.
Niedbala, R. Sam et al., "Detection of marijuana use by oral fluid and urine analysis following single-dose administration of smoked and oral marijuana, " Journal of Analytical Toxicology, vol. 25, Jul./Aug. 2001.
Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.
"N.S. woman who tested positive for pot when she wasnt high to challenge roadside testing laws," CBC Radio, posted Apr. 3, 2019. 6 pages.
Oguma, T., et al., "Clinical contributions of exhaled volatile organic compounds in the diagnosis of lung cancer", PloS one, (Apr. 6, 2017), 12(4):e0174802.
Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.
Ohlsson, Agneta et al., "Single dose kinetics of deuterium labelled delta1-tetrahydrocnnabinol in heavy and light cannabis users," Biological Mass Spectrometry, vol. 9, Issue 1, pp. 6-10, Jan. 1982, abstract.
Olmon RL, Slovick B, Johnson TW, Shelton D, Oh SH, Boreman GD, Raschke MB. "Optical dielectric function of gold", Physical Review B. Dec. 28, 2012;86(23):235147.
Owens, S. Michael et al., I Radioimmunoassay of delta-9-tetrahydrocannabinol in blood and plasma with a solid-phase second-antibody separation method, Clin. Chem. 27/4, 619-624 (1981).

"Owlstone—About", downloaded on Mar. 25, 2019 from https://www.owlstonemedical.com/about/.
"Owlstone—EVOC Probes", downloaded on Mar. 25, 2019 from https://www.owlstonemedical.com/science-technology/evoc-probes/.
"Owlstone—FAIMS technology", downloaded on Mar. 25, 2019 from https://www.owlstonemedical.com/science-technology/faims-technology/.
"Owlstone—Research case studies", downloaded on Mar. 25, 2019 from https://www.owlstonemedical.com/science-technology/research-case-studies/.
"Owlstone Medical—Active Clinical Pipeline", downloaded on Mar. 25, 2019 from https://www.owlstonemedical.com/clinical-pipeline/.
"Owlstone Medical—Products", downloaded on Mar. 21, 2019 from https://www.owlstonemedical.com/products/.
"Owlstone Medical—The Home of Breath Biopsy: A Breathalyzer for Disease", downloaded on Mar. 25, 2019 from https://www.owlstonemedical.com/#.
"Owlstone Medical—The Home of Breath Biopsy: Breath Biopsy—VOC Biomarkers", downloaded on Mar. 25, 2019 from https://www.owlstonemedical.com/#.
Pardon, G, et al., "Aerosol sampling using an electrostatic precipitator integrated with a microfluidic interface", Sensors and Actuators B: Chemical. Feb. 2015, vol. 212, pp. 344-352.
Peel, H.W. et al., "Detection of drugs in saliva of impaired drivers," J Forensic Sci. Jan. 1984;29(1):185-9, PubMed abstract 6366113.
Perez-Reyes, M. et al., "Comparison of effects of marihuana cigarettes to three different potencies," Clin Pharmacol Ther. May 1982;31(5):617-24, PubMed abstract 6280918.
Perez-Reyes, M. et al., "Intravenous injection in man of 9-tetrahydrocannabinol and 11-OH-9-tetrahydrocannabinol," Science. Aug. 18, 1972;177(4049):633-5, PubMed abstract 4558903.
Perez-Reyes, M. et al., "The clinical pharmacology and dynamics of marihuana cigarette smoking," J Clin Pharmacol. Aug.-Sep. 1981;21(8-9 Suppl):201S-207S, PubMed abstract 6271825.
Perez-Reyes, Mario, "Marijuana smoking: factors that influence the bioavailability of tetrahydrocannabinol," NIDA Monograph 1990;99:42.
PerkinElmer Inc., "TSA Signal Amplification (TSA) Systems," Document No. 007703_01, 16 pages, accessed at perkinelmer.com/lab-solutions/resources/docs/BRO_tsasignalamplification systems.pdf.
"Pexa—About PExA", downloaded on Mar. 25, 2019 from http://pexa.se/en/about-pexa/.
"Pexa—Analysis", downloaded on Mar. 25, 2019 from http://pexa.se/en/product-services/analysis/.
"Pexa—Business Concept Vision", downloaded on Mar. 25, 2019 from http://pexa.se/en/about-pexa/business-concept-vision/.
"Pexa—History", downloaded on Mar. 25, 2019 from http://pexa.se/en/about-pexa/history/.
"Pexa—How PExA works", downloaded on Mar. 25, 2019 from http://pexa.se/en/product-services/how-pexa-works/.
"Pexa—Particles in Exhaled Air", downloaded on Mar. 25, 2019 from http://pexa.se/en/.
"Pexa—PExA 2.0", downloaded on Mar. 25, 2019 from http://pexa.se/en/product-services/pexa-2-0/.
"Pexa—Product Services", downloaded on Mar. 25, 2019 from http://pexa.se/en/product-services/.
"Pexa—Product-Sheet", Sep. 2016.
"Pexa—Research & Development", downloaded on Mar. 25, 2019 from http://pexa.se/en/product-services/research-development/.
"Pexa—Research areas", downloaded on Mar. 25, 2019 from http://pexa.se/en/respiratory-research/research-areas/.
"Pexa—Respiratory Research Needs", downloaded on Mar. 25, 2019 from http://pexa.se/en/respiratory-research/.

* cited by examiner

SYSTEMS AND METHODS USING SURFACE-ENHANCED RAMAN SPECTROSCOPY FOR DETECTING TETRAHYDROCANNABINOL

CROSS-REFERENCE TO RELATED APPLICATION

This application claims the benefit of U.S. Provisional Patent Application No. 63/024,423, filed May 13, 2020, which is incorporated herein by reference in its entirety.

TECHNICAL FIELD

The present technology pertains to using Surface-Enhanced Raman Spectroscopy (SERS) for detecting analytes in samples. In particular, but not by way of limitation, the present technology provides systems and methods using SERS for detecting cannabinoids including tetrahydrocannabinol (THC) in breath samples.

BACKGROUND

With legalization of marijuana expanding and the risk of marijuana-associated impaired driving increasing, there is a need for additional methods and devices for determining levels of cannabinoid compound, such as tetrahydrocannabinol (THC) in a subject's sample.

The background description provided herein is for the purposes of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

This summary is provided to introduce a selection of concepts in a simplified form that are further described in the Detailed Description section below. This summary is not intended to identify key features or essential features of the claimed subject matter, nor is it intended to be used as an aid in determining the scope of the claimed subject matter.

The present disclosure relates to using Surface-Enhanced Raman Spectroscopy (SERS) for detecting analytes in samples. Uses can include detection of a cannabinoid using SERS, as well as apparatuses and systems to implement such detection methods. In particular embodiments, detecting can include determining an amount of tetrahydrocannabinol (THC) in a breath sample from a subject.

Accordingly, in a first aspect, the present disclosure encompasses a handheld breath sample apparatus for detection of an analyte in a breath sample SERS.

In some embodiments, the apparatus includes: a housing, in which the housing includes a cartridge interface configured to mechanically interface with a cartridge that has a SERS-active substrate. In particular embodiments, the SERS-active substrate including one or more capture sites for a breath sample.

In some embodiments, the analyte present in the breath sample is absorbed or adsorbed at or in the capture sites. In particular embodiments, the capture site is or includes a metal nanostructure, which in turn is disposed on a surface configured to capture an aerosol drop from a breath sample by impaction.

In some embodiments, a surface of the SERS-active substrate is configured to cause excitement of surface plasmons (e.g., localized surface plasmons) upon exposure to a laser light, thereby enhancing Raman signals and allowing for trace detection of the analyte. In particular embodiments, the analyte is THC or an analog thereof.

In other embodiments, the enhancing of the Raman signals provides a $10^3$ to $10^{10}$-fold signal increase, as compared to traditional "bulk" Raman scattering, by a strong electromagnetic wave coupling of the Raman signals.

In some embodiments, the trace detection of the analyte is single molecule detection of the analyte in the breath sample.

In other embodiments, the SERS-active substrate is configured to facilitate droplet capture through inertial impaction. In one instance, the apparatus further includes an impaction port disposed within the housing, wherein the impaction port has a longitudinal axis that is perpendicular to a major plane of the SERS-active substrate, and wherein the impaction port is configured to be in fluidic communication with the one or more capture sites disposed on a surface of the SERS-active substrate. In yet other embodiments, the SERS-active substrate further includes a detection region (e.g., configured to capture one or more aerosol drops) and a calibration region (e.g., configured to provide a layer of a surfactant present in the aerosol drops).

In some embodiments, the apparatus further include an interface or a laser source configured to optically access the one or more capture sites. In particular embodiments, the interface can be configured to optically couple to a detection device (e.g., in which the interface allows for a spectrometer or detector configured to optically access the capture sites(s) and/or SERS-active substrate(s)).

In a second aspect, the present disclosure encompasses a method using SERS for detection of an analyte in a breath sample. The method can include: determining an amount of analyte captured from a breath sample using SERS using a SERS-active substrate, the SERS-active substrate including one or more capture sites for a breath sample; comparing the determined amount of analyte captured from the breath sample to a threshold level for the analyte in breath; and indicating whether the determined amount of the analyte captured from the breath sample exceeds the threshold.

In some embodiments, the determining an amount of the analyte captured from a breath sample using SERS includes receiving enhanced Raman signals that is $10^3$ to $10^{10}$ fold signal increase, as compared to traditional "bulk" Raman scattering, by a strong electromagnetic wave coupling of the enhanced Raman signals.

In particular embodiments, the analyte is THC or an analog thereof. In some embodiments, the threshold is correlated with a baseline maximum level of THC in breath associated with consumption of THC outside a window of THC-associated impairment. In particular embodiments, the threshold is correlated with an average amount of THC in breath between 2 and 3 hours after inhalation.

In some embodiments, the determining the amount of the analyte captured from the breath sample using SERS allows for single molecule sensitivity.

In further embodiments, the method further includes: wirelessly transmitting data corresponding to the determining an amount of the analyte captured from the breath sample using SERS, the comparing the determined amount of the analyte from the breath sample to the threshold level for the analyte in breath, and the indicating whether or not the determined amount of the analyte captured from the breath sample exceeds the threshold, to a remote location.

In some embodiments, the analyte captured from the breath sample using SERS is captured with a hand-held device.

In a third aspect, the present disclosure encompasses a system using SERS for detection of an analyte in a breath sample. In some embodiments, the system includes: an excitation laser configured to excite a SERS-active substrate, the SERS-active substrate including one or more capture sites for the breath sample; a high sensitivity spectrometer configured to collect one or more Raman signals from the one or more capture sites; and a fiber optic Raman probe electrically connected to the high sensitivity spectrometer.

In some embodiments, the one or more Raman signals are directly proportional to an amount of the analyte captured in the breath sample.

In some embodiments, the excitation laser has an irradiation wavelength from about 500-650 nm (e.g., from 500-600 nm, 550-650 nm, or about 600 nm). In other embodiments, the irradiation wavelength is from about 400-550 nm (e.g., from 400-500 nm, 450-500 nm, or about 488 nm).

In further embodiments, the system includes: a cartridge, wherein the cartridge including the SERS-active substrate including the one or more capture sites for the breath sample.

In any embodiment herein, the analyte is tetrahydrocannabinol (THC) or an analog thereof. Non-limiting analogs can include cannabinol (CBN), cannabidiol (CBD), carboxy THC or 11-nor-9-carboxy-Δ9-tetrahydrocannabinol (THC-COOH), 11-hydroxy-Δ9-tetrahydrocannabinol (11-hydroxy THC), 9-carboxy THC or Δ9-tetrahydrocannabinolic acid (THC-9-COOH), tetrahydrocannabinolic acid (THCA, THC-2-COOH), as well as isomers thereof.

In any embodiment herein, the SERS-active substrate includes one or more metal nanostructures. Non-limiting nanostructures can include metal nanoparticles, such as gold nanoparticles, silver nanoparticles, and/or copper nanoparticles.

Details of one or more implementations of the subject matter described in this specification are set forth in the accompanying drawings and the description below. Other features, aspects, and advantages will become apparent from the description, the drawings, and the claims.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and to explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 4A-4C shows a cross-sectional diagrams of an inertial impaction structure, that can serve as a non-limiting capture site of the breath collection module (BCM). Provided are (A) a diagram of a non-limiting inertial impaction structure, (B) another diagram of a non-limiting inertial impaction structure; and (C) yet another diagram of a non-limiting inertial impaction structure showing an example of a SERS-active substrate.

FIG. 12A-12C are not necessarily drawn to scale.

DETAILED DESCRIPTION

In various embodiments of the present technology, Surface Enhanced Raman Spectroscopy (SERS) is an extension of Raman spectroscopy in which metal structures (e.g., nanoparticles, such as gold or silver nanoparticles) amplify Raman signals. This technique works via an electromagnetic effect where molecules come into proximity with the metal structures. When incident laser light strikes the metal structures or a surface thereof (e.g., a metal nanoparticulate surface), surface plasmons (or localized surface plasmons) are excited, greatly enhancing Raman signals. The enhancement is significant, making SERS capable of trace level detection of molecules or analytes.

SERS-based tetrahydrocannabinol (THC) detection may be performed with urine, blood, or saliva. Breath based detection is typically more difficult, but the capture mechanism of the present technology allows a higher surface density of THC molecules allowing using SERS for detecting THC in breath samples with single molecule detection sensitivity. Furthermore, SERS can allow for label-free detection of analytes, as well as detection of captured, dried samples in some instances. Accordingly, described herein are apparatuses, systems, and methods for capturing breath samples on substrates that facilitate SERS-based detection of analytes.

Figure 1:
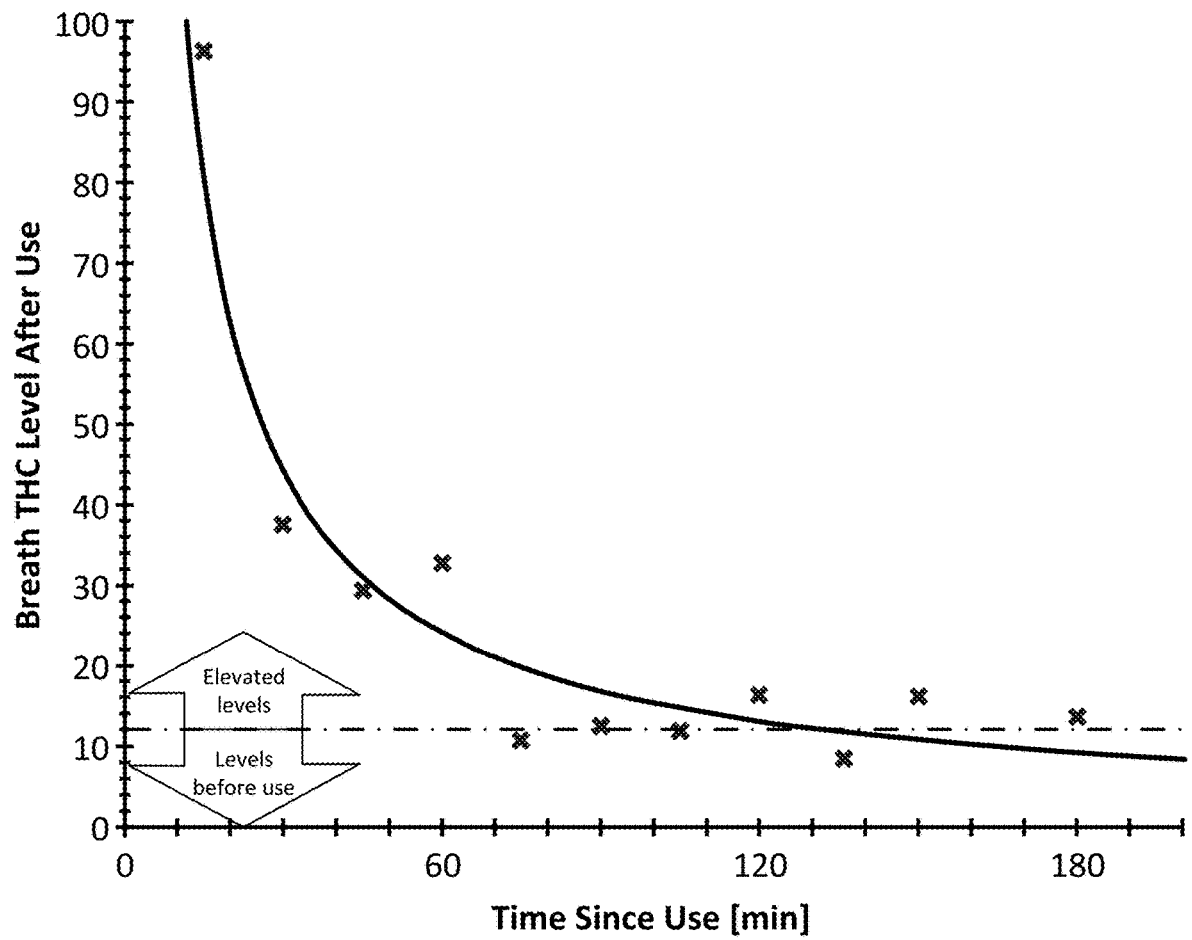
FIG. 1 depicts a plot showing breath THC level vs. time since use.

In particular embodiments, the present disclosure relates to detection in which the analyte is THC or an analog thereof. FIG. 1 depicts a plot showing breath THC level in picograms (pg) per breath (5 L) vs. time in minutes (min) since use in chronic or frequent THC smokers. From the plot it can be seen that THC level in breath drops substantially in the first hour, and after 2 hours it drops below the maximum baseline threshold for chronic users. Testing has determined a maximum baseline THC level in breath for chronic users to be in the picogram per liter of breath range. Based on data obtained through testing, it appears that the threshold may represent a baseline mean level of residual THC in breath associated with consumption of THC across a broad demographic, regardless of use frequency, outside a window from inhalation to between 2 and 3 hours after inhalation, which has been associated with THC impairment. The threshold referenced in the comparison of the disclosed method may be less than 10 picogram/liter (pg/L) of breath, or from 2 to 5 pg/L of breath, or from 2 to 3 pg/L of breath, for example, about 2.4 pg/L of breath. The maximum baseline 12 pg/5 L (2.4 pg/L) breath is superimposed on the plot. The threshold may vary depending upon the capture efficiency of the device or system with which the method is conducted, and can be tuned in practice.

Figure 2:
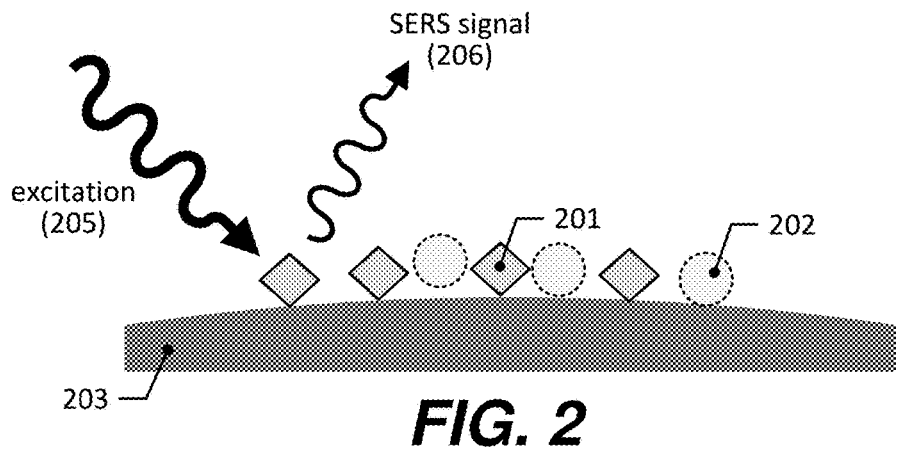
FIG. 2 illustrates a non-limiting embodiment for detecting the presence of an analyte 201 by detecting a Surface-Enhanced Raman Spectroscopy (SERS) signal 206, according to various embodiments of the present technology.

FIG. 2 illustrates a non-limiting embodiment for SERS-based detection of a target analyte 201 (e.g., THC or an analog thereof). In some instances, the target analyte 201 may be associated with other molecules 202, such as surfactants (e.g., phospholipids) that can be present in aerosolized droplets of exhaled breath samples. SERS-based detection can be employed in the presence of such other molecules 202 without necessary interfering with the detection of the target analyte 201.

Non-limiting analytes include THC, as well as other markers, such as cannabinol (CBN), cannabidiol (CBD), carboxy THC or 11-nor-9-carboxy-Δ9-tetrahydrocannabinol (THC-COOH), 11-hydroxy-$\Delta^9$-tetrahydrocannabinol (11-hydroxy THC), 9-carboxy THC or $\Delta^9$-tetrahydrocannabinolic acid (THC-9-COOH), tetrahydrocannabinolic acid (THCA, THC-2-COOH), and similar compounds, as well as isomers thereof.

Turning again to FIG. 2, SERS-based detection includes the use of a SERS-active substrate 203. Herein, the SERS-active substrate is configured to provide a capture site that can interact with the target analyte, as well as to provide a surface that can propagate or cause excitement of surface plasmons. Detailed description of the SERS-based detection and SERS-active substrates are more fully provided herein.

Surface plasmons are generated by providing an excitation radiation 205 to the SERS-active substrate 203, thereby generating a SERS signal 206 that can indicate whether or not the target analyte 201 present. The SERS signal can be analyzed, compared, deconvoluted, processed, or otherwise evaluated to determine the presence of the target analyte. In one instance, the measured SERS signal (e.g., a Raman spectrum) is compared to a signature SERS signal that is associated with the target analyte. Such signatures can include the presence of one or more peaks at certain wavelengths or the presence of certain combinations of peaks at certain intensities and/or wavelengths. In particular embodiments, the SERS signal can provide single molecule detection of the target analyte.

Figures 3A, 3B:
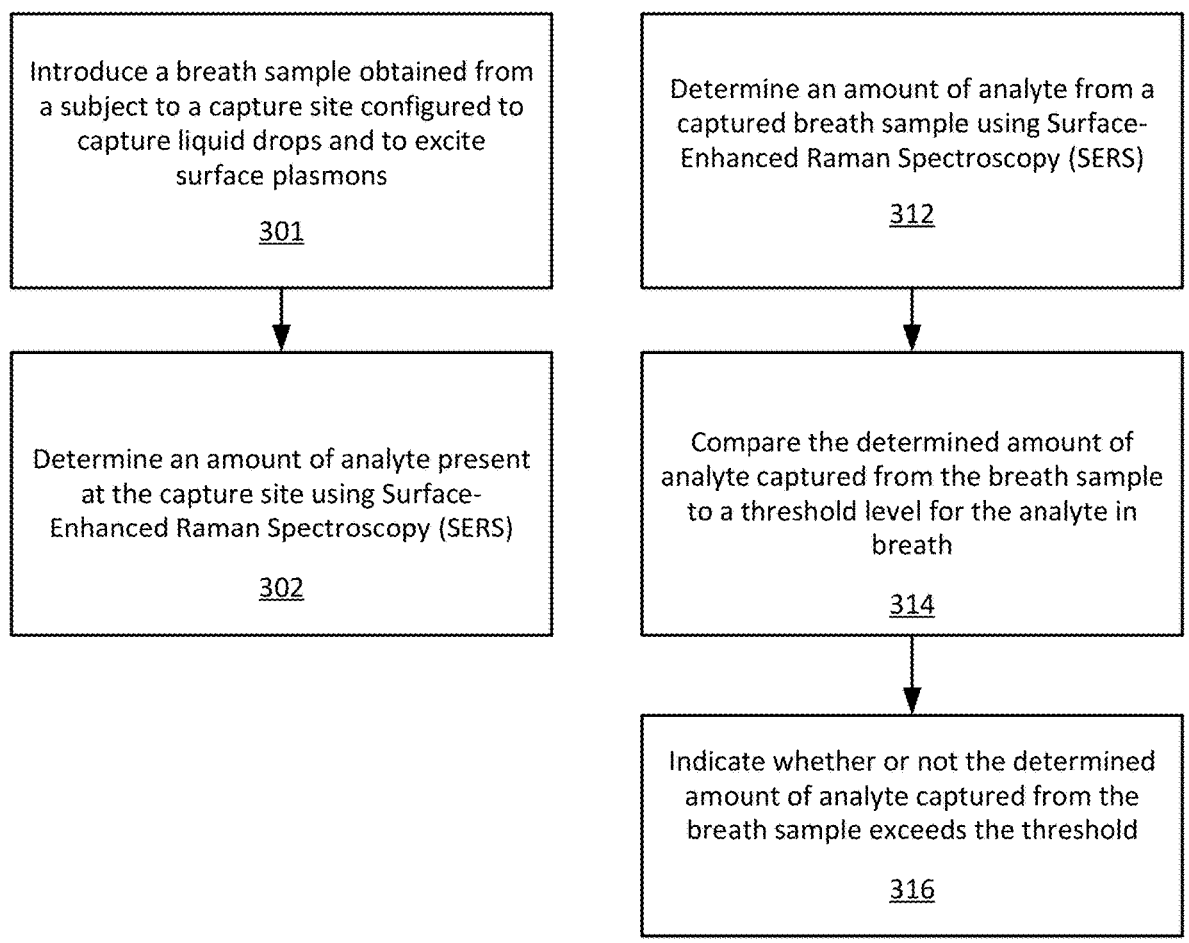
FIG. 3A-3D depicts (A) a non-limiting process flow chart for method in accordance with the present disclosure, (B) another non-limiting process flow chart, (C) yet another non-limiting process flow chart, and (D) a further non-limiting process flow chart.

Referring to FIG. 3A, a general flow chart for a method in accordance with the present disclosure is depicted. According to various embodiments, the method for detection of an analyte can include introducing a breath sample obtained from a subject to a capture site 301; and determining amount of a target analyte present at the capture site using SERS 302. To facilitate use with a breath sample, the capture site can be configured to capture liquid drops (e.g., using a droplet trap, as described herein). To facilitate use of SERS, the capture site can be configured to excite surface plasmons, such as localized surface plasmons. In particular embodiments, the capture site can include one or more metal structures (e.g., metal nanoparticles or other metal nanostructures).

Such methods can also include comparing an amount of analyte to determine whether or not the determined amount exceeds a particular threshold. As discussed herein with reference to FIG. 1, such a threshold may be useful when detecting THC and assessing whether a determined amount of THC in the breath sample is associated with THC impairment. Thus, FIG. 3B shows another general flow chart for a method in accordance with the present disclosure is depicted.

According to various embodiments, the method for detection of an analyte can include determining an amount of a target analyte from a captured breath sample using SERS 312; comparing the determined amount of target analyte captured from the breath sample to a threshold level for the analyte in breath 314; and indicating whether or not the determined amount of target analyte captured from the breath sample exceeds the threshold 316. In some instance, the captured breath sample can be present on a SERS-active substrate having one or more capture sites (e.g., as described herein).

Figure 3C:
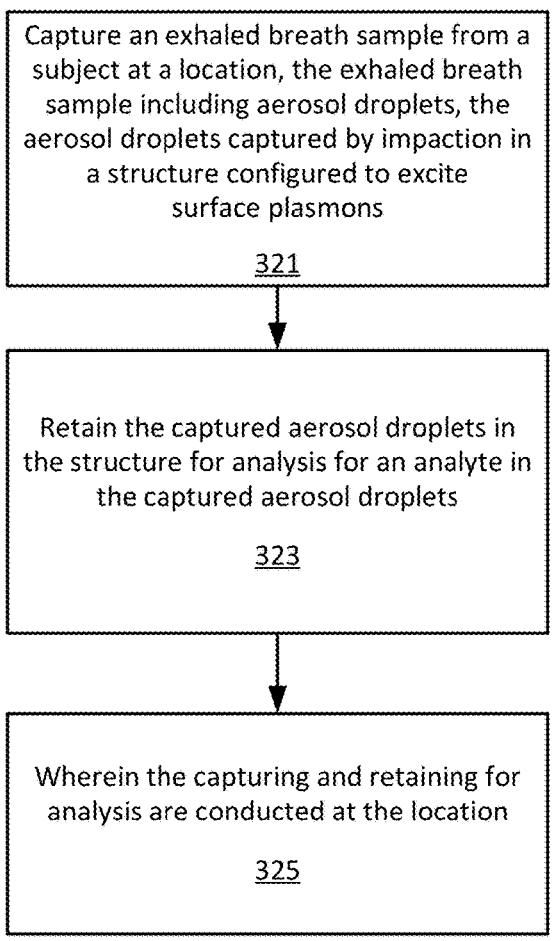
Figure 3D:
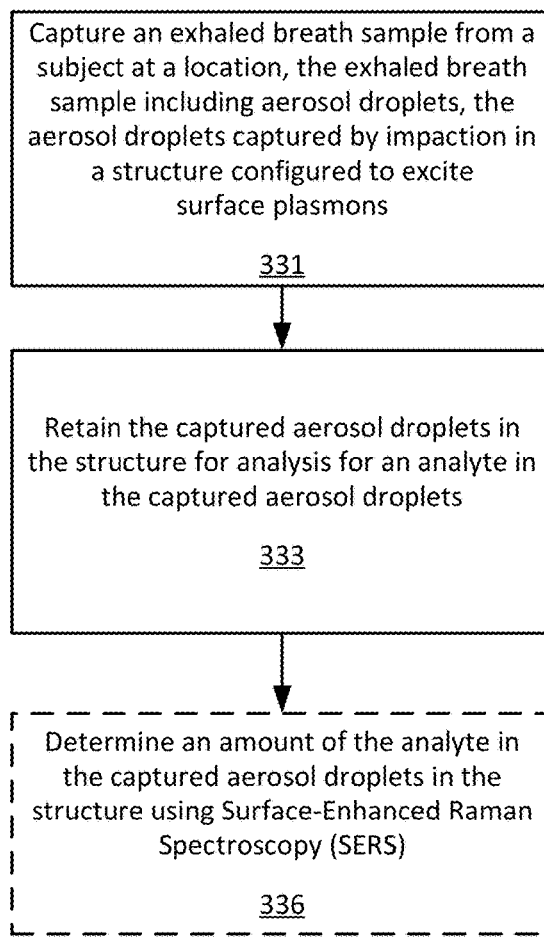

A captured breath sample can be analyzed or stored for later analysis. As seen in FIGS. 3C-3D, some embodiments include a method for capturing an exhaled breath sample in a manner that allows for SERS-based detection at any useful time (e.g., immediately after capture or later). FIG. 3C shows a general flow chart for a non-limiting method that includes capturing an exhaled breath sample from a subject at a location, in which the exhaled breath sample includes aerosol droplets 321; and retaining the captured aerosol droplets in the structure for analysis for an analyte in the captured aerosol droplets 323, wherein the capturing and retaining for analysis are conducted at the location 325. In particular embodiments, the aerosol droplets are captured by impaction in a structure configured to excite surface plasmons (e.g., localized surface plasmons). Such a structure can include a droplet trap, in which the impaction site within the droplet site also includes a surface configured to propagating or exciting surface plasmons for SERS-based analysis. For instance, the surface can include a SERS-active substrate, a metal structure, or a metal nanostructure.

FIG. 3D shows another general flow chart for a non-limiting method that includes capturing an exhaled breath sample from a subject at a location, in which the exhaled breath sample includes aerosol droplets 331; retaining the captured aerosol droplets in the structure for analysis for an analyte in the captured aerosol droplets 333; and optionally determining an amount of the analyte the captured aerosol droplets in the structure using SERS 336. The determining operation 336 can be conducted at the location (in which the capture operation 331 is conducted) or at a different location (e.g., a centralized lab, a forensics lab, etc.).

In any embodiment herein, capturing the aerosolized droplets or liquid drops in a breath sample can include the use of a droplet trap, as described herein. In particular, the droplet trap includes the use of a material that facilitates trapping of aerosol drops. In one embodiment, the droplet trap includes a material, which is provided as a substrate having one or more channels. Of these channels, one or more can be configured to facilitate droplet capture through inertial impaction. Another channel can include at least one passage that provides optical access to the trapped aerosol drop. This passage can, e.g., facilitate delivery of the excitation radiation (e.g., a laser light) to the trapped aerosol drops, as well as collection of SERS signals emanating from the trapped aerosol drops after exposure to excitation radiation. Such a passage can include a free optical path or an optical element (e.g., one or more mirrors, lenses, filters, beam splitters, optical fibers, etc., that can optionally bend or direct radiation signals) to deliver the SERS signal(s) to a spectrometer and/or detector configured to measure or detect a Raman-based signal.

Droplet Traps

Before diving into the design of droplet traps, it is useful to describe the basic mechanism of how aerosol droplets can be captured by inertial impaction. This technique involves driving a stream of fluid (in this case, air from a breath sample) containing the droplets or particles of interest from the impaction port 401 towards a stationary surface of a substrate 402 (or impaction substrate) and through a fluidic passage 410. When the gas streamlines encounter the stationary surface, they turn parallel to the surface (see FIG. 4A). The aerosol or particle droplets, however, have a higher inertia due to their higher densities, and are unable to make the turn necessary to stay with the gas/jet streamlines 405. As a result, they impact the stationary surface of the substrate 402 (e.g., a surface including a SERS-active substrate), where they adsorb onto the stationary surface and are captured at the capture site 403.

The process of inertial impaction is characterized by a universal dimensionless number called the Stokes' number (St), given by:

$$St = \frac{\rho_p d_p^2 v}{9\mu D}$$

where $\rho_p$ is the density of the aerosol droplet or particle, $d_p$ is the diameter of the aerosol droplet, $v$ is the linear velocity of the air stream through the impaction port perpendicular to the impaction surface of the substrate, $\mu$ is the viscosity of the gas stream, and D is the hydraulic diameter of the impaction nozzle/port. For a given Stokes number, there is a capture efficiency ($\eta$) which represents the probability or fraction of particles with the particular Stokes number, that will be captured by the impaction surface.

A plot of capture efficiency versus log(St) typically shows a characteristic sigmoidal behavior for capture efficiency as a function of St. A characteristic property of the relationship between capture efficiency and St is a sharp transition between low and high capture efficiencies. This allows for inertial impaction to act as a binary collector, with very low capture efficiency for St numbers below a certain value and very high capture efficiencies for St above a certain threshold value. If we keep all other parameters fixed except for $d_p$ in the expression for St, then St operates only as a function of the aerosol or particle size, $d_p$. For different values of $d_p$, we obtain different St values, which translates to a particular capture efficiency. Because of the sharp transition in capture efficiency as a function of St, there is a sharp transition in capture efficiency as a function of particle size, or $d_p$. The sharp-transition occurs around a particle size called as the cut-off diameter. An inertial impactor may thus act as a sieve, trapping all droplets above the cut-off diameter, and allowing smaller droplets to pass through completely.

Droplet traps designed for inertial impaction may utilize this strong relationship between St and capture efficiency. Based on this "sieve" property, the trivial solution is to design the droplet trap to capture the smallest droplet size desired, but there are practical limitations; and there is a trade-off between cut-off size and other parameters.

Generally speaking, droplet traps may feature turns and bends to facilitate the capture of droplets of particular size ranges. In the context of a largely planar structure or substrate, such as a microfluidic plate that may be suitable for analyzing collected samples having very small volumes, one particular type of droplet trap may utilize a plurality of small impaction ports that are positioned on an outer major surface (e.g., one of the larger, flat surfaces) of the planar structure. The droplet trap can be configured to interact with a housing, a valve structure, or another intermediary structure, which in turn can be adapted to interface with, for example, a mouthpiece or saliva trap.

In practice, a test subject (person) may place their lips around the mouthpiece or saliva trap to form a generally airtight seal, and may then exhale therethrough and into a device (including into a cavity or plenum within the device). The device may then serve to distribute the air from a person's exhaled breath to the plurality of small impaction ports. Each impaction port may overlap be in fluidic communication with a SERS-active substrate.

Figure 4A:
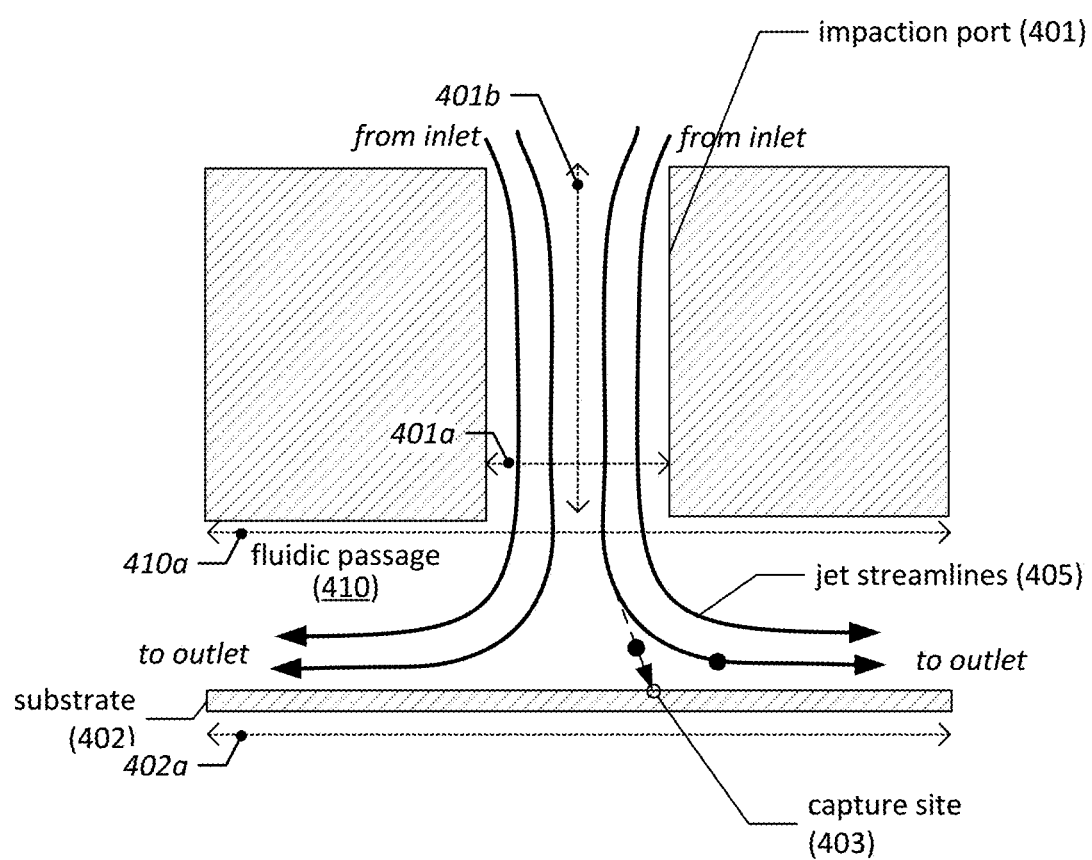

Generally speaking, as seen in FIG. 4A, the impaction port 401, when rectangular or otherwise oblong in nature, may be oriented such that the "short" axis 401a of the impaction port 401 is aligned with a major axis 410a of the fluidic passage 410, as well as with the longitudinal or "long" axis 401b of the impaction port 401 being perpendicular or transverse to this major axis 410a. Such an arrangement can create a thin "sheet" flow of breath sample, which a) constrains the flow paths that the breath sample may follow when traversing the 90° bend to smaller radiuses of curvature (which increase the likelihood that a larger droplet will not be able to make the turn and will impact the floor of the fluidic passage 410) and b) reduces the chance of turbulent flow, which may interfere with efficient droplet capture.

In some embodiments, the impaction port can have a longitudinal axis 401b that is perpendicular to a major plane (along axis 402a) of a SERS-active substrate 402. Furthermore, the impaction port can be configured to be in fluidic communication with the one or more capture sites 403 disposed on a surface of the SERS-active substrate.

Figures 4B, 4C:
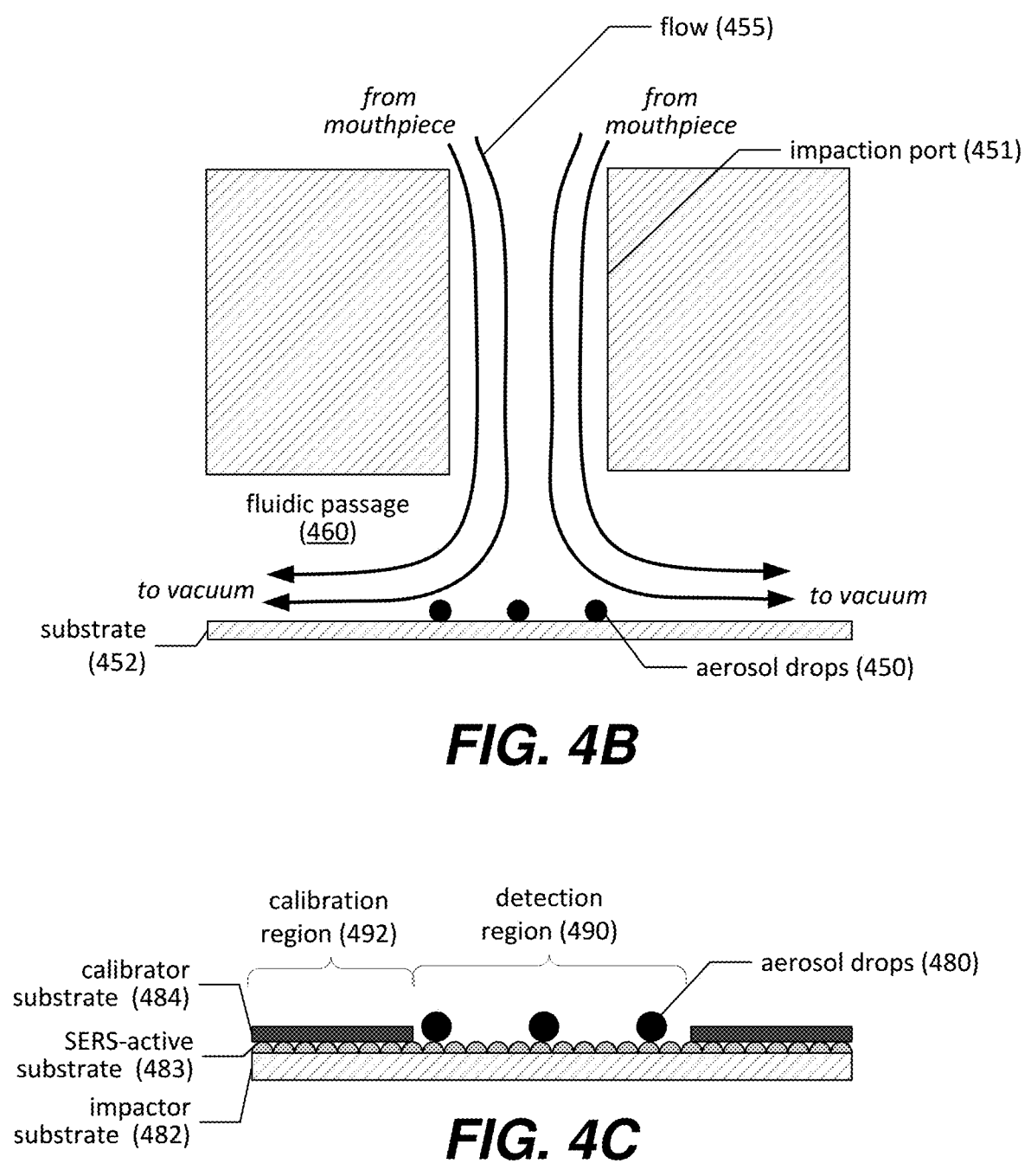

FIG. 4B shows yet another embodiment of a droplet trap. As can be seen, the droplet trap can include an impaction port 451 disposed within a housing or a substrate disposed within the housing. This impaction port 451 can provide fluidic communication to a further substrate 452, which serves to provide one or more capture sites for aerosol drops 450. Fluidically disposed between the impaction port 451 and the substrate 452 can be a fluidic passage 460, which is connected to a vacuum, thereby establishing flow 455 from an inlet (e.g., from the mouthpiece) to an outlet (e.g., a vacuum).

The substrate 452 can be configured to facilitate capture of aerosol drops, as well as to allow for detection of analytes within the drops. Accordingly, the substrate can include an impactor substrate (or an impactor surface) in conjunction with a SERS-active substrate (or a SERS-active surface). The configuration of such substrates and surfaces can be such to provide effective droplet capture, which can provide both enhanced concentration of analytes and minimized distance between the analyte and the SERS-active surface to provide increased SERS signals.

FIG. 4C shows a non-limiting substrate can include integrated structures, such as a substrate having an impactor substrate 482 disposed beneath the SERS-active substrate 483. The SERS-active substrate can include any useful metal nanostructures described herein. In use, aerosol drops 480 are captured on the SERS-active substrate 483. In particular embodiments, a calibrator substrate 484 (or calibrator surface) can be included as an internal calibrator for SERS signals. In one instance, the calibrator substrate can include a deposited surfactant layer, which can provide a calibration signal upon exposure to a laser light to provide a calibrated SERS signal. In one instance, the calibration signal is used to normalize a SERS-signal, thereby providing a normalized SERS-signal indicative of the presence of the analyte (without significant contribution by the presence of the surfactant present in the calibrator surface). Accordingly, the integrated substrate may include a detection region 490 configured to capture aerosol drops and facilitate detection of analyte(s) and a calibration region 492 configured to provide calibration signals.

The calibrator substrate (or calibrator surface) can include any molecules that are present in control breath samples but not present in analyte-positive samples (e.g., positive samples being those that possess an amount of analyte that exceeds a threshold level of the analyte in breath). Such molecules can include those present in aerosol drops, such as surfactants (e.g., one or more lipids, phospholipids, and proteins). Non-limiting surfactants can include dipalmitoyl phosphatidylcholine (DPPC), palmitoyl-oleoyl phosphatidylcholine (POPC), surfactant protein A (SP-A), mucin, cholesterol, and the like, as well as combinations thereof. In particular embodiments, the calibrator substrate can be composed of one or more layers of surfactants. Such layers can include monolayers, bilayers, multilayers, as well as any useful combinations or plurality of such layers. In one embodiment, the integrated substrate includes an impactor substrate, a SERS-active substrate disposed on a top surface of the impactor substrates, and one or more calibrator substrates (e.g., including a deposited DPPC monolayer, bilayer, or multilayer) disposed on a portion of a top surface of the SERS-active substrate.

Figure 5:
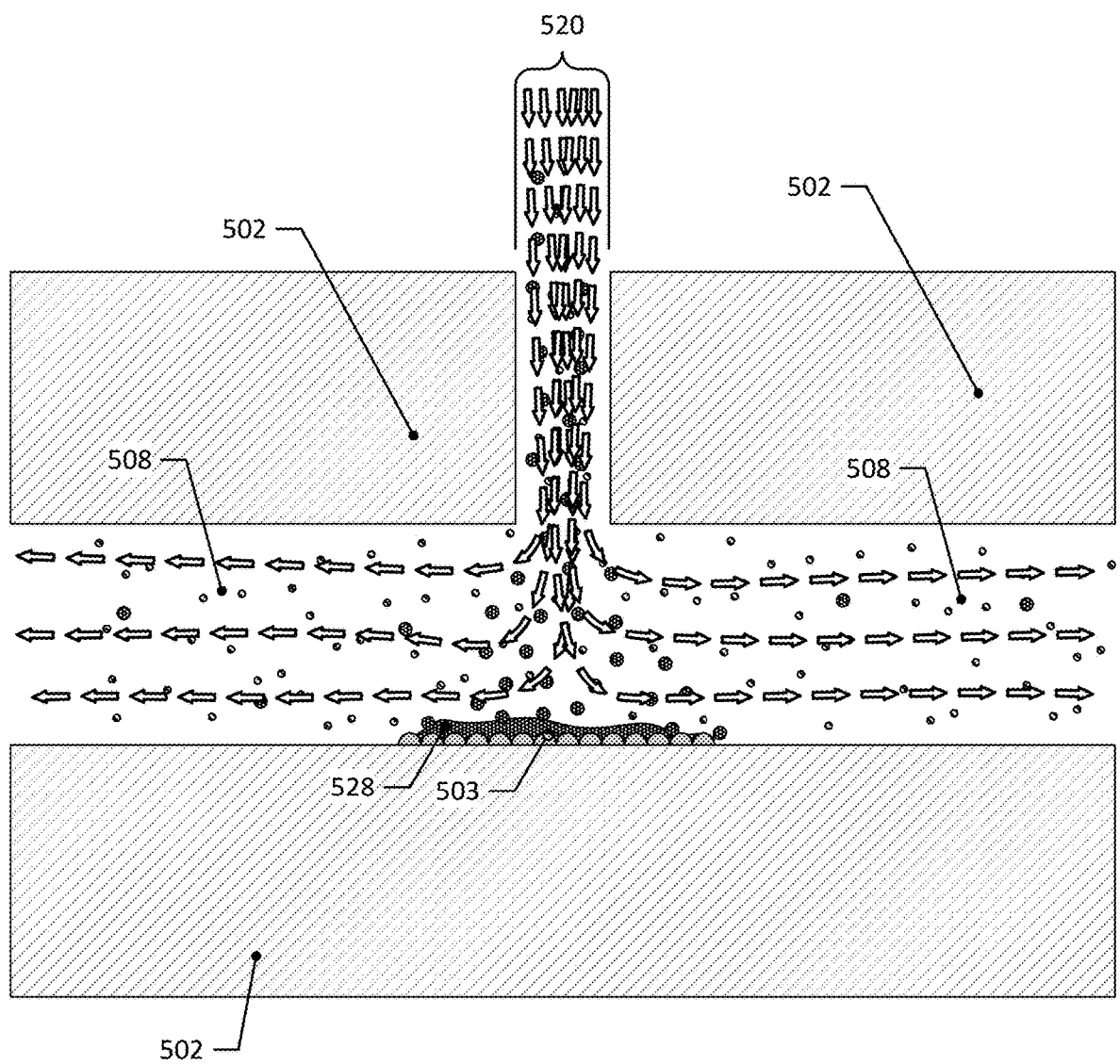
FIG. 5 depicts a cross-section view of a portion of a droplet trap.

The droplet trap may include one or more impaction ports located along a path of the gas/jet streamline. FIG. 5 depicts a cross-section view of a portion of a droplet trap. As can be seen, the impaction port 520 extends through a substrate 502 and intersects with the fluidic passage 508. Breath sample that flows through the impaction port 520 may enter the fluidic passage 508 and then make a 90° turn (arrows are added to indicate the general flow directions of the breath sample). Smaller particles (droplets), indicated by smaller-sized circles with lighter shading, in the breath sample flow may successfully navigate the 90° turn, whereas larger particles/droplets, indicated by larger-sized circles with darker shading, will generally not be able to make the 90° turn and will impact the floor of the fluidic passage 508 and adsorb onto it, forming a trapped portion of sample 528.

The fluidic passage can also be designed to include capture sites 503, in which the location of such capture sites 503 can be configured to capture liquid drops, as well as to capture any analytes associated with such liquid drops. To facilitate detection of analytes by employing SERS, the capture site(s) can further include a SERS-active substrate, such as any described herein.

In some embodiments, the capturing of the aerosol droplets by impaction involves capturing of the droplets through a plurality of impaction ports that are fluidically connected in parallel.

Capture by impaction provides a versatile approach that is readily adaptable to the capture of analytes including THC in breath. Breath borne analytes have been found to exist primarily in a non-volatile state in aerosolized droplets formed in the deep lung. As a result, the capture target is aerosolized droplets that can be viewed as particles having a an aerodynamic behavior based almost entirely on their size and shape, rather than the particular chemical or other affinity properties of an analyte of interest, as would be the case for a volatile target species. Since the capture is primarily based on the size of the aerosol droplets in the exhaled breath sample, the capture device or apparatus may be configured in the same or similar manner to capture virtually any analyte, by impaction. Then, the detection methodology may be tailored to the particular analyte(s) of interest in the aerosolized droplets captured by impaction, as further described below.

The described methods, devices and systems also have the merit of high yield capture of the component of an exhaled breath sample containing the analytes of interest, namely the aerosolized droplets originating in the deep lung. By contrast, alternative prior or potential methods of detecting breath-borne analytes have relied on affinity methodologies optimized for collection of volatile species in breath, or collection of breath condensate samples. Affinity-based collection techniques have low yield since breath borne analytes have been found to primarily be in non-volatile form and so with limited to no availability for affinity-based collection. Further, affinity-based collection of analytes requires very specific chemical or immunological targeting of the species to be collected, which limits the generality of the approach. Breath condensate collection, on the other hand, while general, lacks the specificity of capture by impaction and so provides a sample this is much less concentrated in and focused on the analytes of interest. This is a substantial impediment when attempting to meaningfully and reliably detect and measure very small quantities of analyte, such as exist in breath.

Described methods, devices and systems have the merits of sample capture by impaction and/or in a point of care format.

Design of a droplet trap or a breath capture module (BCM) begins with considerations on source and form of the target analyte in breath. With the exception of volatile small molecules, all other small molecules and macromolecules are present in breath encapsulated in aerosolized liquid drops in the range of about 0.5 µm-10 µm. The composition of the liquid drops consists primarily of water with other macromolecules associated with the respiratory tract.

For aerosolized liquid droplet targets, a mechanism of capture based on inertial impaction may be particularly effective, and a BCM may be designed with channels incorporating turns and bends to facilitate droplet capture through inertial impaction, as discussed herein. A two-stage mechanical filtering system may be used in some implementations to help screen out droplets that are larger and/or smaller than a desired size range of droplets. For example, a saliva trap, such as saliva traps used with blood alcohol sensors, may be placed upstream of an inertial impaction droplet trap to filter out droplets that are larger than the upper end of the desired size range, e.g., larger than 100 µm, and the inertial impaction droplet trap may then be used to filter out those smaller droplets that pass through the saliva trap but are larger than the lower end of the desired size range, e.g., larger than 0.1 µm. The droplets that are captured by the inertial impaction droplet trap may generally be of the desired size range and be analyzed in situ or ex situ, such as in a system configured to interface with a device including the droplet trap.

In addition to the channel geometry, substrate material used for the fabrication of droplet traps may be selected, in some implementations, based on the properties of the target of interest. For molecular capture, the substrate material may be chosen such that the target has an affinity for the surface of the material and is immobilized on that surface after contact. The material may also facilitate release of the target into solution during elution or assay steps. Generally, the material may be weakly hydrophilic for a hydrophilic target and weakly hydrophobic for a lipophilic target. In other embodiments, the material can facilitate enhanced SERS-based detection, such as by including one or more SERS-active substrates, metal structures, etc.

However, for various non-volatile aerosolized species discussed in this disclosure, the BCM material may be designed to capture liquid drops, the primary constituent of which is water. For hydrophilic targets, a weakly hydrophilic substrate will enable retention of liquid drops during capture while facilitating release of these drops during elution or reaction steps. For hydrophobic targets, a strongly hydrophilic surface will discourage the target from adhering to the surface during elution or reaction steps. Macromolecules, particularly large proteins, are amphiphilic, which means they consist of both hydrophobic and hydrophilic regions. A hydrophilic capture material is appropriate for these molecules as well. In some embodiments, metal structures (e.g., surfaces of metal structures) can be treated to provide hydrophobic and/or hydrophilic regions. Such treatments can include use of oxidation, acid treatment, silanization, and the like, such as described herein.

In addition to surface characteristics, e.g., hydrophobicity or hydrophilicity of the material used for the sample collection sites of the droplet trap, analysis systems or other structures that interface with the droplet trap may be designed to facilitate efficient retrieval of or access to collected samples.

Typical captured droplets from exhaled breath may include a high percentage (>50% by mass) of surfactants such as phospholipids, such as DPPC (dipalmitoyl phosphatidylcholine). These surfactants may include long-chain aliphatic carboxylic acids which render them highly lipophilic. When aerosol droplets are captured on a surface, due to the extremely low volumes (pL or less) of droplets, the water contained in these droplets can evaporate very quickly (especially considering the flow of exhaled air that flows past them during droplet capture), resulting in a concentrated patch or "scab" of lipophilic surfactants on the surface(s) of the capture sites in the droplet trap. It is within these "scabs" that the analytes of interest may be trapped.

As discussed above, surface modifications, e.g., surface treatments to render the surfaces on which the "scabs" form more or less hydrophilic or hydrophobic, may be used to increase or enhance the recovery of collected sample material.

Surface modification may be used to create a surface which prevents phospholipids from forming a "scab" on the surface of the droplet trap (or at least from forming a "scab" that is strongly adhered to that surface). Potential modifications include coating the surface with polymers such as tri-block copolymers containing repeating ethylene oxide and propylene oxide groups or biological macromolecules such as proteins (examples include an albumin, such as bovine serum albumin (BSA), casein, etc.). In these two cases, the mechanism of deposition of the surface treatment may be physical adsorption, wherein the coating agent is allowed to incubate with, for example, a surface of the SERS-active substrate having the capture sites, and the agent is allowed to adsorb onto the surface, forming a barrier. Alternately, the surface can be treated chemically to impart specific functionality. Silanizing is one such method of surface treatment. In this process, a silanizing agent such as trichloro silanol may be allowed to react with the surface (or alternately air) to form a silanized coating on the surface. The silanized coating can create a barrier between the phospholipids and the plastic surface.

In some cases, the analyte may be present in alveolar lining fluid (ALF) which is present in exhaled breath as aerosolized droplets, for which a geometry (of the droplet trap) based on inertial impaction can produce high capture efficiency. A hydrophilic material may be used for capturing these droplets. Suitable materials for such a droplet trap may include polystyrene, polyethylene terephthalate (PET), PETG (glycol modified version of polyethylene terephthalate), glass, etc. A droplet trap with a hydrophilic material (treated polystyrene, PETG, glass, etc.) in a geometry designed for inertial impaction may provide good capture of droplets/particles of interest.

A droplet trap for capture aerosol drops via inertial impaction may be designed, according to the principles and concepts outlined herein, to intercept aerosol particles >0.7 µm, for example, and retain them on the walls of a channel through which breath is flowed while the droplet trap is used to collect a breath sample. Multiple impaction sites may be incorporated into the droplet trap to provide for parallel capture of droplets, thereby allowing for higher droplet capture efficiency and greater breath throughput.

In addition to flow considerations, a handheld design may, in some instances, also facilitate specific breathing profiles such as rapid inhalation, rapid exhalation, coughing, etc. to stimulate production of volatiles or aerosol drops from appropriate regions of the respiratory tract. This can be accomplished, for example, using sensors such as pressure, flow rate, and $CO_2$ sensors to monitor breath sample collection.

Fluidic communication, as the phrase is used herein, refers to a state in which two or more volumes are connected by one or more passages, orifices, or other features such that fluid may flow between them. Generally speaking, the phrase should be understood to imply that there is some form of structure providing the fluidic communication, rather than just exposure to the ambient environment. For example, two open-topped buckets positioned side-by-side in upright positions would not be considered to be in "fluidic communication" (even though fluid, e.g., gas, could conceivably waft of diffuse from one bucket to the other), whereas placing an end of a hose into each of those same two open-topped buckets would cause the buckets to be viewed as being in "fluidic communication" with each other since there is structure that serves to provide a fluid flow passage between them.

SERS-Based Detection

Surface-Enhanced Raman Spectroscopy (SERS) combines Raman scattering and Surface Plasmon Resonance (SPR). SERS uses SPR to enhance surface sensitivity of Raman scattering resulting in a large enhancement of a Raman scattered signal. For example, SERS results in a $10^3$ to $10^{10}$-fold signal increase compared to traditional "bulk" Raman scattering. The present technology provides systems and methods using SERS for detecting analytes (e.g., cannabinoids including tetrahydrocannabinol (THC)) for label-free THC detection in breath samples. The present technology in some embodiments provides systems and methods using SERS for detecting THC with single molecule detection sensitivity. The systems, methods and contemplated devices of the present technology may also be adaptable to combining testing for THC and alcohol (ethanol) impairment, and/or to the detection of other airborne substances, including controlled substances, and breath-borne indicators of various disease states and viruses.

Raman scattering or the Raman effect is the inelastic scattering of input electromagnetic radiation (e.g., photons) by matter in various embodiments. Such inelastic scattering is dependent on the type of matter or molecule with which it interacts, such that the Raman scattering signal (output) can be used to gain information about that matter or molecule. Stokes Raman scattering arises from vibrational energy being gained by a molecule as incident photons are shifted to a lower energy.

Furthermore, Raman scattering requires a change in polarizability, and allowable Raman transition states require different molecular polarizability of those states. A polarized molecule will oscillate at the same frequency as an input electric field (E) of an electromagnetic wave:

$$P = \varepsilon_0 \chi E,$$

wherein P is the polarization density, $\varepsilon_0$ is the electric permittivity in vacuum, and $\chi$ is the electric susceptibility.

Molecules also have vibrational modes. Electric susceptibility will oscillate at the vibrational energy modes of a molecule. Thus, an induced dipole moment will be modulated by vibrational oscillations of the molecule:

$$P = \underbrace{\alpha_0 E_0 \cos(2\pi v_0 t)}_{\text{Rayleigh scattering}} + \left(\frac{\partial \alpha}{\partial Q} \frac{Q_0 E_0}{2}\right) \left\{ \underbrace{\cos[2\pi(v_0 - v_{vib})t]}_{\text{Stokes scattering}} + \underbrace{\cos[2\pi(v_0 - v_{vib})t]}_{\text{anti-Stokes scattering}} \right\},$$

wherein $\alpha$ is the polarizability of the molecule, $\alpha_0$ is the polarizability at equilibrium, $E_0$ is the amplitude of the electromagnetic wave, $v_0$ is the frequency of the electromagnetic wave, $v_{vib}$ is the vibrational frequency of the molecule, Q is a bond length at any instant, and $Q_0$ is a maximum displacement distance of atoms relative to their equilibrium position.

Figure 6:
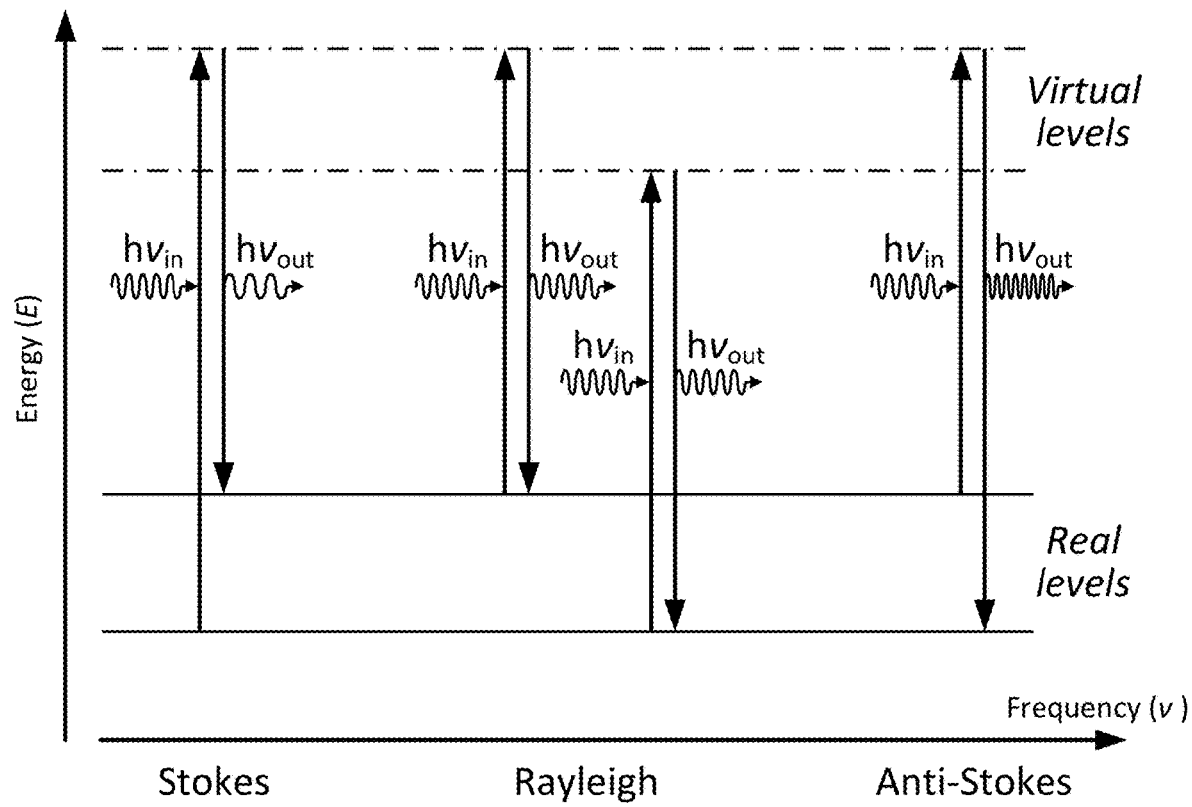
FIG. 6 illustrates an example of an energy diagram showing Rayleigh scattering and Raman scattering (Stokes and anti-Stokes).

Raman scattering is conceptualized as involving a virtual electronic energy level, which corresponds to the energy of the exciting laser photons. Absorption of a photon excites the molecule to the imaginary state, and re-emission leads to Raman or Rayleigh scattering. In all three cases, the final state has the same electronic energy as the starting state but is higher in vibrational energy in the case of Stokes Raman scattering, lower in the case of anti-Stokes Raman scattering, or the same in the case of Rayleigh scattering. FIG. 6 provides a basic Quantum Mechanics (QM) description of Raman scattering, which includes a photon exciting the molecule to the imaginary state for Stokes Raman scattering, Rayleigh scattering, and anti-Stokes Raman scattering.

The following illustrates an equation for a Raman signal, according to various embodiments of the present technology:

$$I \propto I_0 N \sigma,$$

wherein I is the intensity of the Raman signal, $I_0$ is the incident optical irradiance [w cm$^{-2}$], N is the number of molecules, and $\sigma$ is the Raman scattering cross section. As can be seen, the Raman signal is proportional to concentration of a molecule to be detected (i.e., number of molecules). For example, a Raman signal can be proportional to the number of molecules of THC in a breath sample. Other factors that can influence the intensity for a Raman signal include excitation/collection optics efficiency, background signals, and the like.

Figure 7:
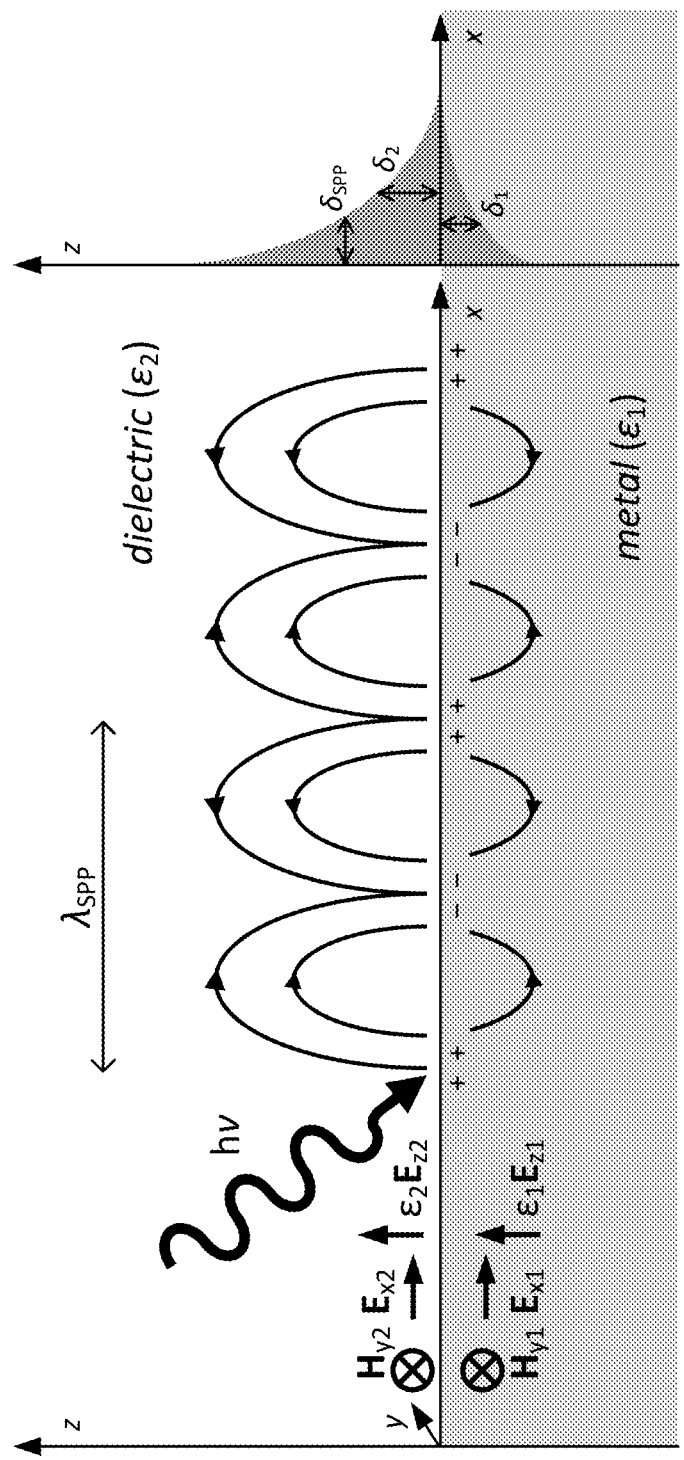
FIG. 7 illustrates an example of a surface plasmon at an interface between a metal (having permittivity $\varepsilon_1$) and a dielectric (having permittivity $\varepsilon_2$), which can be employed for Surface Plasmon Resonance (SPR) according to various embodiments of the present technology.

FIG. 7 illustrates a review of Surface Plasmon Resonance (SPR), according to various embodiments of the present technology. SPR is the resonant oscillation of conduction electrons at the interface between negative and positive permittivity material stimulated by incident light. SPR is a fundamental principle behind embodiments of the present technology and is the basis of many tools for measuring adsorption of material onto planar metal (e.g., typically gold or silver) surfaces or onto the surface of metal nanoparticles (e.g., gold or silver nanoparticles). Electromagnetic (EM) waves incident at a metal-dielectric boundary can create a coherent, surface wave having a wavelength $\lambda_{SPP}$, as shown in FIG. 7. For example, electron oscillation at the surface, as a result of the interaction between light and free electrons, can propagate a surface wave at the metal-dielectric interface along axis x.

SPR only exists when certain requirements are met at an interface of two materials. In one instance, a specific combination of dielectric constants ($\varepsilon$) can be provided, such as between a metal having $\varepsilon_1$ and a dielectric material having $\varepsilon_2$ that is a positive real dielectric constant (and having no imaginary part, such as for air or insulating materials). In another instance, the interface is characterized by having negligible bulk effects, such as can be present by a sufficiently thin layer (along axis z) that can sufficiently propagate a surface wave with negligible influence by a bulk material disposed beneath a surface layer. Furthermore, an EM wave must decay in a direction normal to surface (i.e., as an evanescent wave).

The characteristics of SPR can be highly dependent on other factors, such as the following: dielectric properties of the materials at the interface; wavelength, angle and polarization of excitation; a thickness of the metal layer (e.g., bulk effects may hinder SPR); and/or the roughness of the surface on the order of nanometer scale.

Resonance condition occurs at the right wavelength and angle. In various embodiments, the resonance condition is characterized by a strong absorption of light at the right excitation wavelength and at the right excitation angle. Furthermore, a small change in dielectric properties of the insulating medium may result in a large signal change. Moreover, SPR has a high sensitivity to changes at the interface (e.g., due to binding of an analyte such as THC). In one instance, such changes at the interface can provide a detectable shift in wavelength of the resonance peak.

Figure 8A:
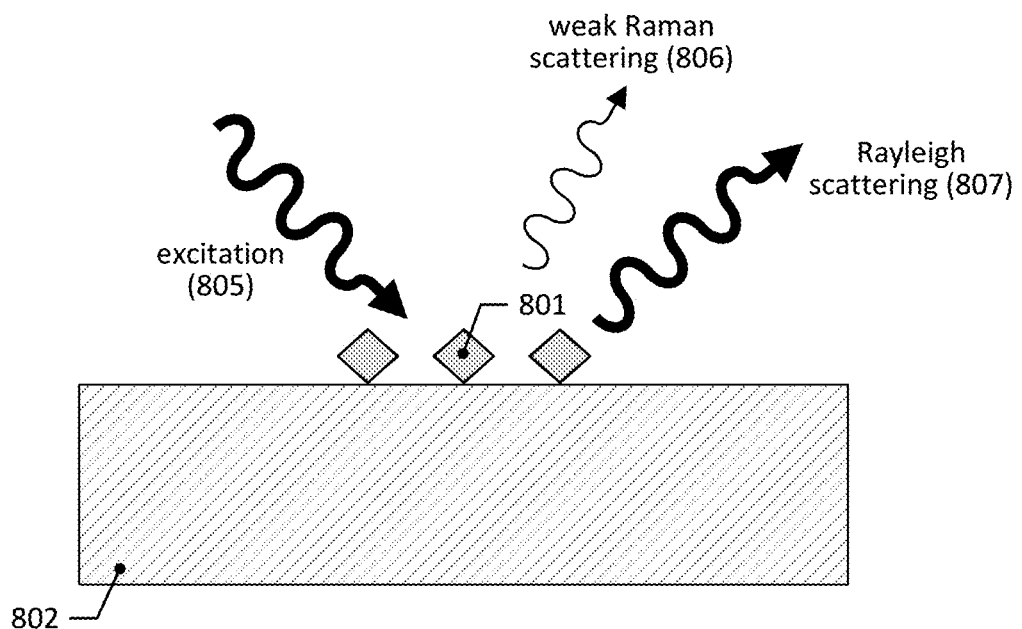
FIG. 8A-8B shows the extent of Rayleigh and Raman scattering in the presence of an analyte at (A) a first interface and (B) at a second interface for use in Surface-Enhanced Raman Spectroscopy (SERS), according to various embodiments of the present technology.
Figure 8B:
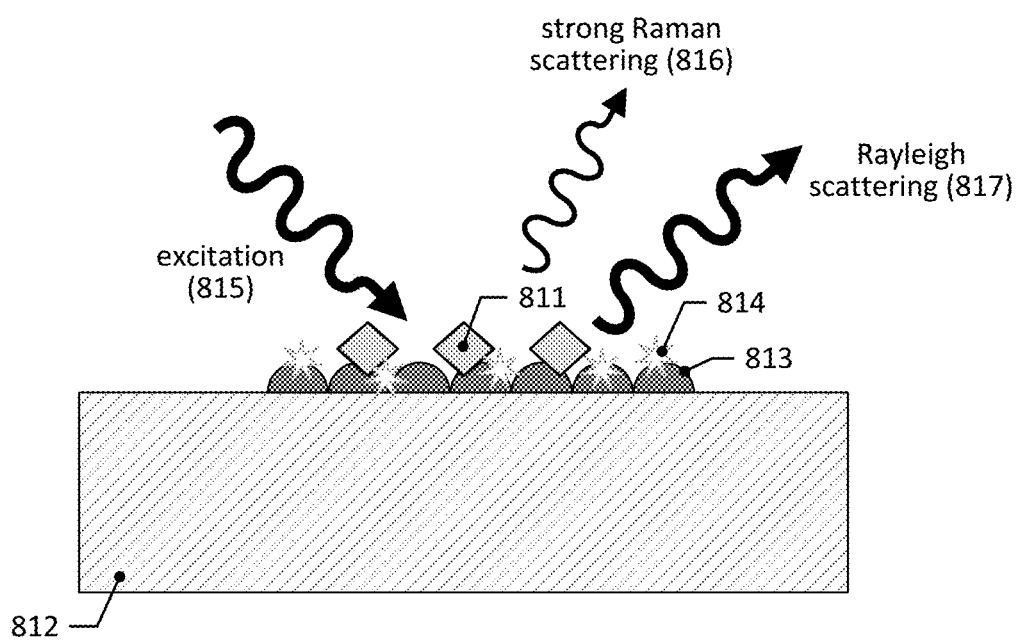

Surface-Enhanced Raman Spectroscopy (SERS) generally employs localized surface plasmon resonance (LSPR) to generate enhanced Raman signals. FIG. 8A-8B shows the effect of using SERS, according to various embodiments of the present technology. In FIG. 8A, a weaker Raman scattering 806 is shown, as compared with a stronger Raman scattering 816 shown in FIG. 8B. For instance, in FIG. 8A, the analyte 801 is disposed on a planar surface of a substrate 802, in which the excitation radiation 805 provides weak Raman scattering 806 in conjunction with Rayleigh scattering 807.

In contrast, FIG. 8B provides an analyte 811 disposed on a surface of a substrate 812 having metal structures 813 (e.g., metal nanostructures), in which the excitation radiation 815 provides stronger Raman scattering 816 in conjunction with Rayleigh scattering 817. If a Raman active molecule 811 (e.g., THC) is present in the vicinity of Localized Surface Plasmon Resonance (LSPR) and concentrated light 814, then strong EM wave coupling can enhance the Raman signals. Raman wavelengths must be close to the SPR wavelength for SERS, and the molecule must be within the decay distance of the electromagnetic enhancement. The enhancement factor depends on dielectric properties, as well as geometry. The enhancement factor can be influence by both EM wave enhancement and chemical enhancement for SERS. See, e.g., Vahimaa P et al., "*Surface-Enhanced Raman Spectroscopy (SERS),*" Institute of Photonics at the University of Eastern Finland, accessible at sway.com/s/XtgAoh8F5QewSEFL/embed, which is incorporated herein by reference in its entirety.

Figure 9:
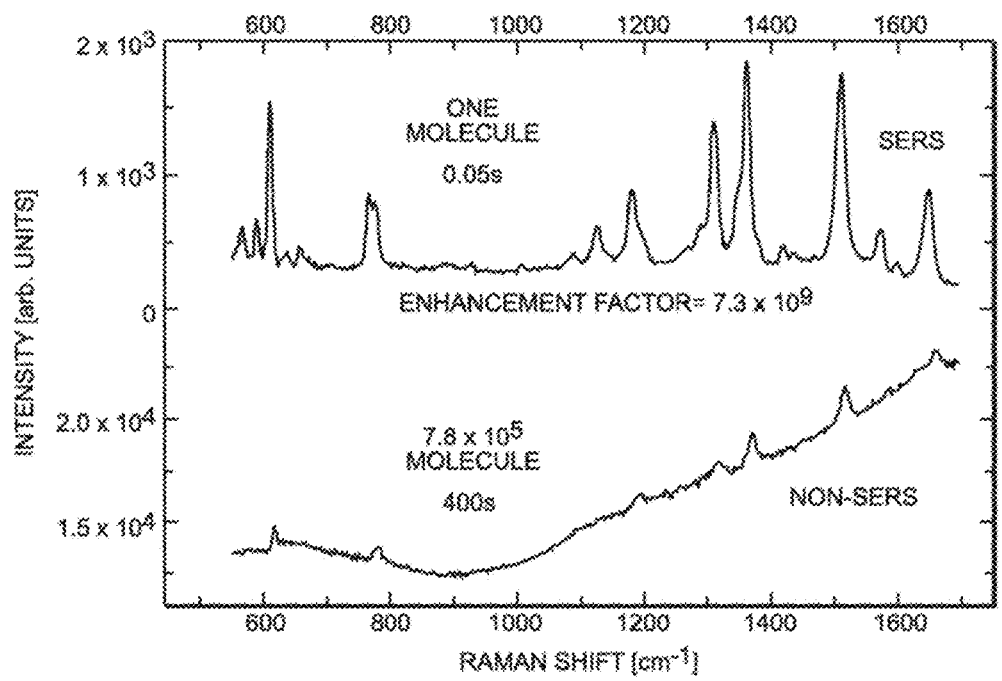
FIG. 9 illustrates enhanced sensitivity of Surface-Enhanced Raman Spectroscopy (SERS) compared with "bulk" Raman scattering, according to various embodiments of the present technology.

FIG. 9 illustrates an example of enhanced sensitivity of Surface-Enhanced Raman Spectroscopy (SERS), as compared with "bulk" Raman scattering, according to various embodiments of the present technology. In FIG. 9, Raman shift vs. intensity is shown comparing a SERS method with a non-SERS method for rhodamine 6G that was excited at 633 nm with a 3 mW incident laser. In this non-limiting example, SERS provided single molecule sensitivity, as compared with $7.8 \times 10^5$ molecules for non-SERS methods, e.g., see E. C. Le Ru E C et al., "*Surface Enhanced Raman Scattering Enhancement Factors: A Comprehensive Study,*" *J. Phys. Chem. C*, 111, 13794-13803 (2007) (hereinafter "Le Ru et al."), which is incorporated herein by reference in its entirety; and in which FIG. 1, FIG. S1, and associated text in Le Ru et al. are incorporated herein by reference, especially as it relates to SERS and non-SERS Raman signals, determination of differential cross-sections, assessment of single molecule (SM) SERS events, and analysis of SM enhancement factor (SMEF).

Figure 10:
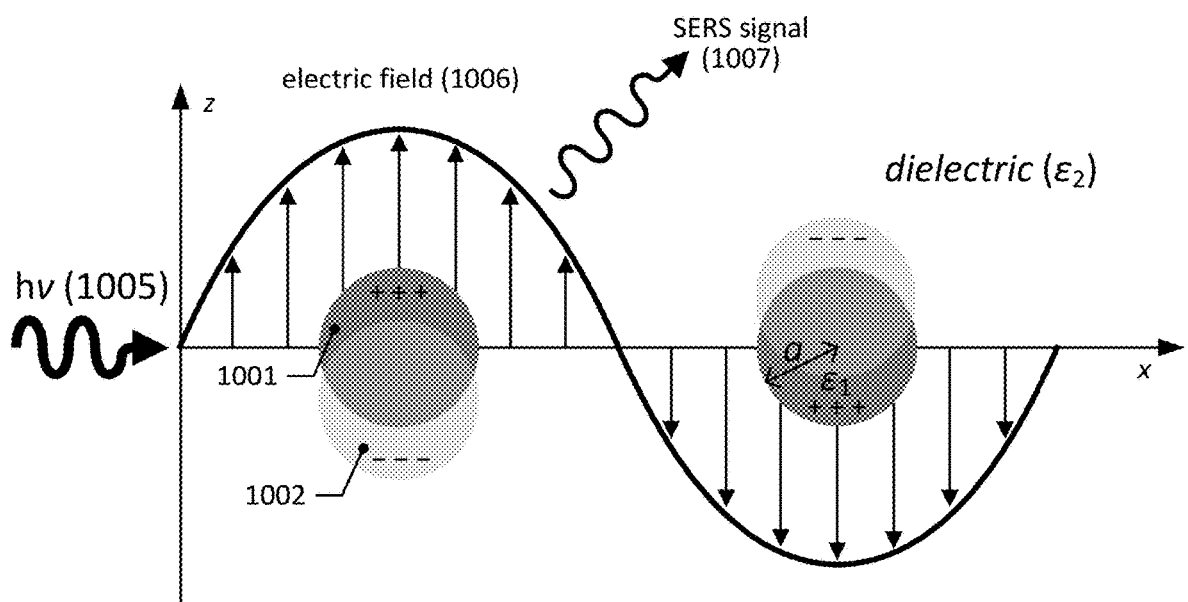
FIG. 10 illustrates a spherical model for Surface-Enhanced Raman Spectroscopy (SERS), according to various embodiments of the present technology.

FIG. 10 illustrates a spherical nanoparticle model for SERS, according to various embodiments of the present technology. As can be seen, the LSPR can be characterized by a collective oscillation of valence electrons (electron cloud 1002) for a metal nanoparticle 1001 that is in resonance with the frequency of incident light 1005. The resultant electromagnetic field 1006 outside the particle has an analytical solution, in which maximum enhancement of the SERS signal 1007 occurs under certain conditions (e.g., $\varepsilon_1 \approx -2\varepsilon_2$). In another embodiment, the extent of SERS enhancement leading to single molecule sensitivity is due to a variety of factors such as nanoparticle size (e.g., having a radius a), shape, material (e.g., having a dielectric constant $\varepsilon_1$), configuration, and the like. See, e.g., Stiles P L et al, "*Surface-Enhanced Raman Spectroscopy,*" *Annu. Rev. Anal. Chem.*, 1, 601-626 (2008) (hereinafter "Stiles et al."), which is incorporated herein by reference in its entirety; in which FIG. 1 and associated text in Stiles et al. are incorporated herein by reference, especially as it pertains to the discussion regarding localized surface plasmon resonance; in which FIG. 2 and associated text in Stiles et al. are incorporated herein by reference, especially as it pertains to the discussion regarding $E^4$ enhancement; and in which FIG. 4 and associated text in Stiles et al. are incorporated herein by reference, especially as it pertains to the discussion regarding instrumentation, nanofabrication, and optimized surface-enhanced Raman spectroscopy surfaces.

As discussed herein, metal materials are of particular use in SERS-active surfaces, and the dielectric constant of such materials can affect the extent of maximizing the enhancement factor (EF). In one instance, EF can be maximized by maximizing g:

$$g = \frac{\varepsilon_1 - \varepsilon_2}{(\varepsilon_1 + 2\varepsilon_2)},$$

wherein $\varepsilon_1$ is the dielectric constant for the metal particle and $\varepsilon_2$ is the dielectric constant of the external environment. Using the equation above, g can be maximized by having $\varepsilon_1 \approx -2\varepsilon_2$. Assuming that a particular breath sample includes DPPC in the external environment in conjunction with the target analyte, the dielectric constant of DPPC can be considered as $\varepsilon_2$. In one non-limiting consideration, $\varepsilon_2$ for DPPC can be between 2 to 4.5 (e.g., from 2 to 4, 2.2 to 4.2, 3 to 3.5, or about 3.2). See, e.g., Gramse G et al, "*Nanoscale Measurement of the Dielectric Constant of Supported Lipid Bilayers in Aqueous Solutions with Electrostatic Force Microscopy,*" *Biophys. J.*, 104, 1257-1262 (2013) (hereinafter "Gramse et al."), which is incorporated herein by reference in its entirety; and in which FIG. 4 and associated text in Gramse et al. are incorporated herein by reference, especially as it relates to experimental capacitance gradient approach curves and fitting parameters to characterize such data, including parameters such as the dielectric constant for the lipid bilayer (e.g., a dielectric constant $\varepsilon_{r,DPPC}$ of about 3.2).

By assuming a value (or range of values) for $\varepsilon_2$, a metal material can be selected under conditions to provide a dielectric constant for the metal ($\varepsilon_1$) that is approximately $-2\varepsilon_2$. The dielectric constant for a metal can be dependent on the irradiation wavelength or photon energy, and the dielectric constant (as a function of wavelength and composed of real and imaginary parts) can be characterized in any useful manner. For instance, the dielectric function of gold (Au) in the visible spectral region can be characterized by spectroscopic ellipsometry measurements or other useful measurements, see, e.g., Olmon R L et al., "*Optical dielectric function of gold,*" *Phys. Rev. B* 86, 235147 (2012) (hereinafter "Olmon et al."), which is incorporated herein by reference in its entirety; and in which FIG. 3 and associated text in Olmon et al. are incorporated herein by reference, especially as it relates to the dielectric function of Au (the negative real part $-\varepsilon 1$) in the visible spectral region for evaporated (EV), template-stripped (TS), and single-crystal (SC) gold samples, and as it relates to variables that can be determined by fitting the data in FIG. 3 to a solution of the Drude-Sommerfeld model or to a Drude dielectric function; and in which FIG. 4 and associated text in Olmon et al. are incorporated herein by reference, especially as it relates to the dielectric function of Au (the imaginary part $\varepsilon_2$) in the visible spectral region for EV, TS, and SC gold samples, and as it relates to variables that can be determined by fitting the data in FIG. 4 to a solution of the Drude-Sommerfeld model or to a Drude dielectric function.

In another instance, the dielectric function of silver (Ag) in the visible spectral region can be characterized by spectroscopic ellipsometry measurements or other useful measurements, see, e.g., including the negative real part and the imaginary part, according to various embodiments of the present technology. See Yang H U et al, "*Optical dielectric function of silver,*" *Phys. Rev. B* 91, 235137 (2015) (hereinafter "Yang et al."), which is incorporated herein by reference in its entirety; and in which FIG. 3 and associated text in Yang et al. are incorporated herein by reference, especially as it relates to the negative real part of the dielectric function of silver (−ε1) in the visible/ultraviolet spectral range for template stripped (TS) silver samples, and as it relates to variables that can be determined by fitting the data in FIG. 3 to a solution of the Drude-Sommerfeld model or to a Drude dielectric function; and in which FIG. 4 and associated text in Yang et al. are incorporated herein by reference, especially as it relates to the imaginary part of the dielectric function of silver (ε2) in the visible/ultraviolet spectral range for TS samples, and as it relates to variables that can be determined by fitting the data in FIG. 4 to a solution of the Drude-Sommerfeld model or to a Drude dielectric function.

By assuming a value (or range of values) for $\varepsilon_2$ for the external environment, a metal material can be selected under conditions to provide a dielectric constant for the metal ($\varepsilon_1$) that is approximately $-2\varepsilon_2$. In one embodiment, the external environment in proximity to the analyte is considered to be DPPC, the metal material includes gold, and the irradiation wavelength is selected to be from about 500-650 nm (e.g., from 500-600 nm, 550-650 nm, or about 600 nm). In some embodiments, the EF is from about $10^3$-$10^6$. In another embodiment, the external environment in proximity to the analyte is considered to be DPPC, the metal material includes silver, and the irradiation wavelength is selected to be from about 400-550 nm (e.g., from 400-500 nm, 450-500 nm, or about 488 nm). In yet other embodiment, the EF is from about $10^5$-$10^8$.

The equation below illustrates the distance dependence for SERS, in which the SERS signal is maximized when the target analyte is absorbed to the enhancing surface, according to various embodiments of the present technology:

$$I_{SERS} = \left(\frac{a+r}{a}\right)^{-10},$$

wherein a is the average size of the field-enhancing features on the SERS-active substrate and r is the distance from the surface to the adsorbed analyte, see, e.g., Stiles et al., which is incorporated herein by reference, and in which section 2.3 in Stiles et al. is incorporated herein by reference, especially as it relates to the distance dependence of SERS.

Figure 11A:
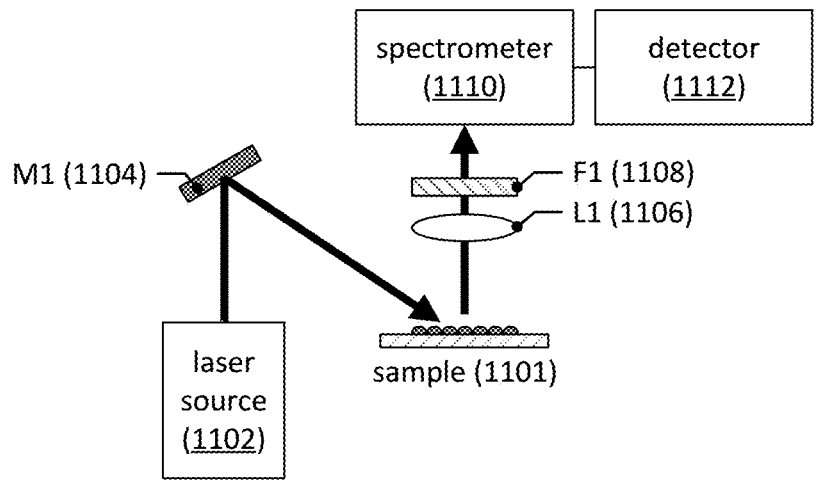
FIG. 11A-11B illustrates exemplary systems and instrumentation for Surface-Enhanced Raman Spectroscopy (SERS) including (A) a first experimental setup and (B) a second experimental setup, according to various embodiments of the present technology.
Figure 11B:
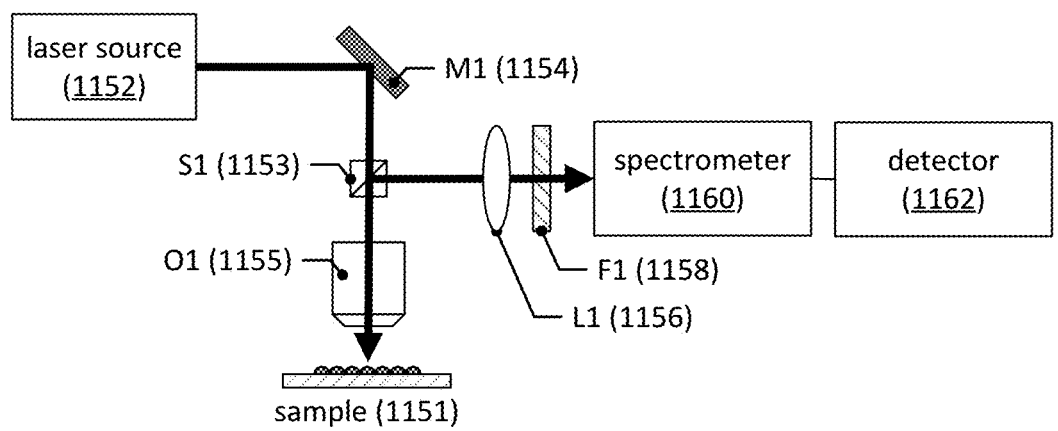

FIG. 11A-11B illustrates exemplary systems and instrumentation for SERS, according to various embodiments of the present technology. FIG. 11A-11B illustrates two instrumental approaches to the measurement of SER spectra. The first approach shown in FIG. 11A is for a non-limiting macro-Raman configuration. Here, a laser source 1102 is focused on the SERS-active substrate having the sample 1101 at a glancing angle by way of a mirror M1 1104. After irradiation, the resulting SERS signal (Raman signal) light is collected by way of a lens L1 1106 (e.g., a collection lens). The light can then be filtered by way of filter F1 1108 (e.g., a notch filter) and delivered to the entrance slit of a spectrometer 1110 and detected using a detector 1112, e.g., a liquid-nitrogen-cooled charged-coupled device camera. The instrumental approach shown in FIG. 11A is, in some instances, used in low spatial resolution and high raw SERS intensity. Nonetheless, such a configuration can be adapted for high resolution and/or low raw SERS intensity signals.

Any optical path herein (e.g., from a laser source to the sample and/or from the sample to the spectrometer or detector) can include any useful optical element to direct, split, focus, filter, and/or process a radiative signal. Non-limiting optical elements include one or more mirrors, fibers, splitters, lenses, filters, objectives, and the like, which can include mechanical or electronic forms thereof. In a particular instance, the optical path can include use of optical fiber, an optical probe, or other elements, which can include miniaturized configurations for use with a handheld apparatus. In some instances, a spectrometer, a detector, or both can be employed.

For higher spatial resolution, a micro-Raman configuration can be used, e.g., as shown in FIG. 11B. Irradiation (or laser light) from a laser source 1152 can be directed to the sample 1151 by way of a mirror M1 1154, in which the light is both focused and collected through the same high numerical aperture objective O1 1155 before delivery to the sample 1151. After, the scattered light is passed through a filter F1 1158 (e.g., a notch filter) for the removal of Rayleigh-scattered light. A beam splitter S1 1153 can be employed between the laser source 1152 and the spectrometer 1160. Additionally, the light can be focused by a lens L1 1156 and directed to a spectrometer 1160 and/or a detector 1162. See, e.g., Stiles et al., which is incorporated herein by reference in its entirety; and in which FIG. 4 and associated text in Stiles et al. are incorporated herein by reference, especially as it pertains to the discussion regarding instrumentation.

SERS can be employed for detection of THC molecules, according to various embodiments of the present technology. In one instance, SERS-based detection can be employed to provide spectra of THC molecules (at various concentration, e.g., $10^{-3}$, $10^{-5}$, $10^{-7}$, $10^{-9}$, and $10^{-12}$ M) on a SERS-active substrate, in which the SERS interface is gold and air. In one embodiment, the intensity of the SERS signal ($I_{SERS}$) at 1603 cm$^{-1}$ is correlated to a concentration of THC in the sample. In another embodiment, the SERS signal is obtained from a range of 1500-1700 cm$^{-1}$, in which the signal in this range is correlated to a concentration of THC in the sample. In yet other embodiments, the SERS signal is obtained from at least one of about 1000, 1030, 1195, 1201, 1275, 1279, 1283, 1323, 1370, 1377, 1382, 1405, 1450, 1546, 1556, 1580, 1595, 1603, 1621, and 1651 cm$^{-1}$. See, e.g., Sivashanmugan K et al., "*Trace Detection of Tetrahydrocannabinol in Body Fluid via Surface-Enhanced Raman Scattering and Principal Component Analysis,*" *ACS Sensors*, 4, 1109-1117 (2019) (hereinafter "Sivashanmugan et al."), which is incorporated herein by reference in its entirety; and in which FIGS. 2A-2B and associated text in Sivashanmugan et al. are incorporated herein by reference, especially as it relates to the SERS spectra of THC molecules on a plasmonic-biosilica SERS substrate and to associated SERS peaks at 1000, 1030, 1201, 1275, 1323, 1370, 1450, 1556, 1580, and 1603 cm$^{-1}$; and in which FIG. 3A-3D, FIGS. 4A-4D, and associated text in Sivashanmugan et al. are incorporated herein by reference, especially as it relates to the SERS spectra of THC molecules in complex fluids on a plasmonic-biosilica SERS substrate and to associated SERS peaks at 1195, 1279, 1283, 1323, 1377, 1382, 1405, 1546, 1595, 1603, 1621, and 1651 cm$^{-1}$.

In various embodiments, a SERS-active substrate includes or is Ag nanoparticles in diatom photonic biosilica. Furthermore, the sample may be dried onto substrate, and detection having a sensitivity to about 1 pM has been demonstrated. Furthermore, different solvents (e.g., methanol, plasma, saliva, alveolar fluid, lung epithelial fluid, lung aspirate, aerosol drops, surfactants, water, and the like, as well as combinations thereof) may be used.

The apparatuses and devices herein can be employed with a system for using SERS for detection of THC molecules, according to various embodiments of the present technology. In one embodiment, the exemplary system can include a high sensitivity spectrometer, an excitation laser or diode source (e.g., a 670 nm excitation source, a 600 nm excitation source, a 488 nm laser excitation source, or any other excitation source of any wavelength described herein), a Raman probe (e.g., optic Raman probe), and/or a detector. Such systems can include any other useful optical elements to optically access the sample, the SERS-active substrate, or a portion thereof. Optical elements can include one or more mirrors, lenses, fibers, filters, wave plates, as well as any described herein.

SERS-active substrates include those having any material that can sustain and propagate surface plasmons, including localized surface plasmons. In one instance, the material include nanostructured metal, including metal nanoparticles (e.g., core-shell particles, solid particles, etc.), nanowires, nanotubes, nanoantennas, nanogratings, nanopillars, nanowrinkles, nanorods, nanocapsules, nanospheres, nanoprisms, nanocubes, nanostars, and nanosheets. See, e.g., Wang A X et al., *"Review of Recent Progress of Plasmonic Materials and Nano-Structures for Surface-Enhanced Raman Scattering," Materials,* 8, 3024-3052 (2015) (hereinafter "Wang et al."), which is incorporated herein by reference in its entirety; and in which FIGS. 4A-4D and associated text in Wang et al. are incorporated herein by reference, especially as it relates to plasmonic nano-structures and metallic nanomaterials with different geometric morphologies. A nanostructure can include any structure having a feature size (e.g., length, width, height, radius, diameter, circumference, gap, periodic distance, etc.) that is from about 0.1-100 nm.

Such nanostructures can be provided in any useful assembly, e.g., as a monolayer, a packed layer, a packed volume, a sheet, a colloid, a colloidal crystal, etc. Such nanostructures can be disposed on a surface of a substrate in any useful manner, such as by patterning, deposition, growth, laser treatment, drilling, lithography, etc. Non-limiting substrates can include a semiconductor material (e.g., silicon or a dielectric, such as silicon nitride), graphene, glass, diatoms, and the like. In one instance, the nanostructures provide a nanostructured surface. In various embodiments multiple types of surfaces are used for SERS including nanoparticles, "roughened" thin films by laser ablation, nanoholes, nanospheres, and nanowires. Each of the surface types used for SERS produces a different enhancement factor, as well as efficiency of capturing the sample. Furthermore, other practicality factors include reproducibility, limitation of laser excitation power, fluorescence, and Raman background from the surface, as well as the shelf-life and environmental stability.

Figure 12A:
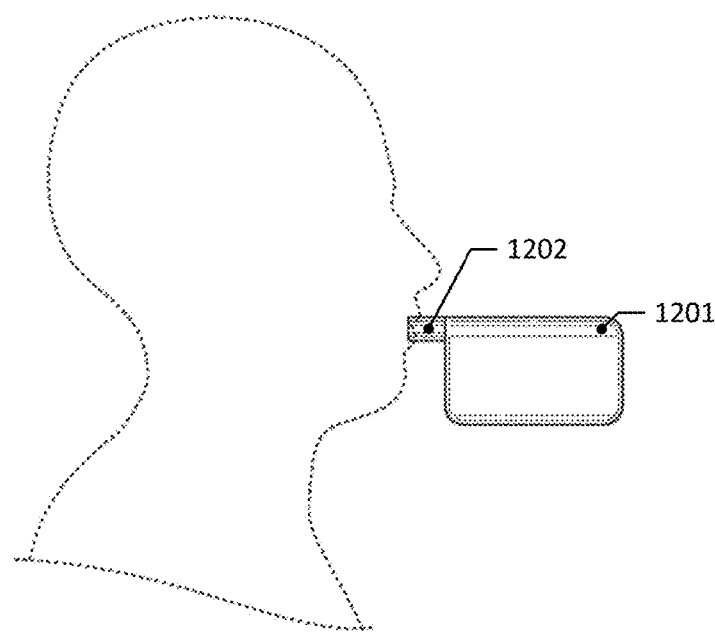
FIG. 12A-12C illustrates (A) a view of an exemplary breath capturing device in use by a subject and cross-sectional views of (B) a non-limiting device and (C) another non-limiting device for use with Surface-Enhanced Raman Spectroscopy (SERS) for detecting trace levels of molecules including cannabinoids such as tetrahydrocannabinol (THC) in breath samples, according to various embodiments of the present technology.
Figure 12B:
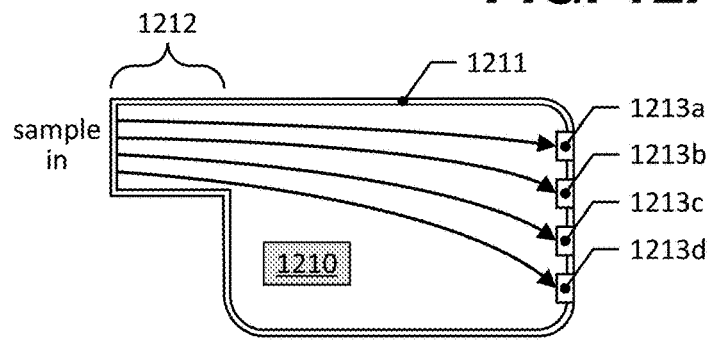
Figure 12C:
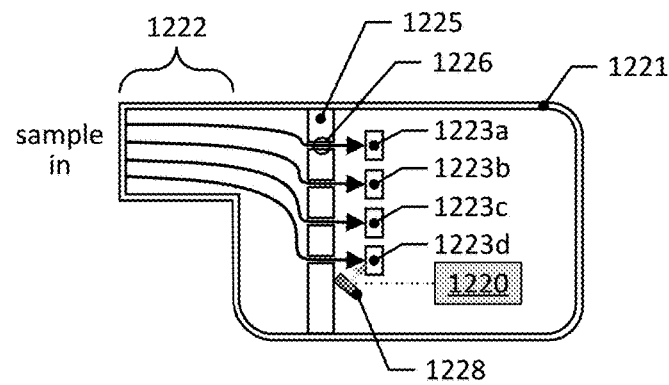

FIG. 12A-12C illustrates an exemplary breath capturing device using SERS for detecting trace levels of molecules including cannabinoids, such as THC in breath samples, according to various embodiments of the present technology. FIG. 12A shows a subject being tested using a breath capture device 1201 by exhaling through a mouthpiece 1202.

FIG. 12B also shows a non-limiting cross-sectional view of breath capturing device. In some embodiments, a breath sample goes inside the breath capturing device by way of a subject breathing through a mouthpiece 1212, which can be a portion of the housing or be a separate structure (e.g., a separate detachable structure). Inside of the housing 1211, the device comprises breath sample capture sites on a SERS-active substrate. Each of portions 1213*a/b/c/d* can each be a SERS-active substrate, such that the device includes a plurality of SERS-active substrates. Alternatively, each of portions 1213*a/b/c/d* can each be a capture site, in which capture sites 1213*a/b/c/d* can be disposed on a single SERS-active substrate or different SERS-active substrates. For example, local breath sample capture sites can be disposed on a surface of the SERS-active substrate. The substrate may comprise metal nanoparticles, a nanoparticulate metal surface (e.g., surface of gold or silver nanoparticles), or any other nanostructured metal described herein. The location of each capture site and/or SERS-active substrate can be configured to optimally capture a breath sample, aerosol drops from a breath sample, and the like (e.g., by way of impaction). In particular embodiments, the capture site and/or SERS-active substrate are configured to be easily removed from the housing, thereby facilitating ex situ analysis or storage for later analysis.

In particular embodiments, the SERS substrate causes localized surface plasmons to be excited, greatly enhancing Raman signals. The enhancement can be significant, making SERS capable of trace level detection of molecules allowing using SERS for detecting THC in breath samples with single molecule detection sensitivity. The device can also comprises an optical detection device 1210 (e.g., a spectrometer or detector configured to optically access the capture sites(s) and/or SERS-active substrate(s)) or an interface 1210 configured to optically couple to a detection device (e.g., in which the interface allows for a spectrometer or detector configured to optically access the capture sites(s) and/or SERS-active substrate(s)).

Optical coupling or optical access, as the phrase is used herein, refers to a state in which two or more areas or volumes are connected by an optical path or one or more optical elements (e.g., any herein) or other features such that an optical signal (e.g., light) may travel between them. This phrase should be understood to imply that one or more structures may be present to provide optical coupling or optical access or that an ambient environment (e.g., air) that facilitates travel of light may also be envisioned.

FIG. 12C shows a cross-sectional view of another non-limiting breath capturing device. The device includes a housing 1221 and a mouthpiece 1222, which can be a portion of the housing or be a separate structure (e.g., a separate detachable structure). Inside of the housing 1221, the device comprises breath sample capture sites on a SERS-active substrate. Each of portions 1223*a/b/c/d* can each be a SERS-active substrate, such that the device includes a plurality of SERS-active substrates. Alternatively, each of portions 1223*a/b/c/d* can each be a capture site, in which capture sites 1223*a/b/c/d* can be disposed on a single SERS-active substrate or different SERS-active substrates.

The device can further include a plate 1225 or another structure having impaction ports 1226 disposed therein. Such a plate (or another structure) can be disposed within the main volume within the housing 1221 or within the narrower volume within the mouthpiece 1222. As can be seen, one or more of the impaction ports 1226 can serve to direct the fluid flow, such that the breath sample is captured by way of impaction on a capture site/SERS-active substrate 1223*a/b/c/d*. The location of each capture site/SERS-active substrate 1223*a/b/c/d* within the housing 1221, from the impaction ports 1226, from the mouthpiece 1222, etc., can be optimized to provide effective droplet separation and/or droplet capture.

The device can also comprises an optical detection device 1220 or an interface 1220 configured to optically couple to a detection device, as well as one or more optical elements 1228 to provide optical access to the capture site/SERS-active substrate 1223a/b/c/d. Non-limiting optical elements are described herein.

The devices and apparatuses herein can be employed within a breath sampling and analysis system. In one instance, the system can include three main components—a base station, a handheld unit, and a cartridge (e.g., a disposable cartridge). In another instance, the system can include two main components—a base station and a handheld unit. In yet another instance, the system only includes a handheld unit.

Furthermore, when a cartridge is present, a handheld unit may be connected with the cartridge in order to collect a breath sample, as the handheld unit can be small, relatively lightweight, and easily wielded by whomever is obtaining the breath sample. The cartridge may then be removed from the handheld unit, and both elements can be separately docked in the base station in order to perform the analysis and report out the results. The cartridge can include the captured sample disposed on the capture sites and the SERS-active substrate. While the functionality of the cartridge could be combined with a handheld unit, although doing so may complicate cleaning and re-use of the handheld unit.

Optionally, the handheld unit can include an integrated SERS-active substrate including the capture sites, such that a cartridge is not required. In this embodiment, the handheld unit can then be docked into the base station for analysis, in which the optical interface of the handheld unit is optically coupled to the base station. Alternatively, the handheld unit can include an integrated detector. For example, the base station and the handheld unit could be combined into one device, although the resulting apparatus would not be as portable as the handheld unit and obtaining a breath sample using such an apparatus would likely require extra effort on behalf of the subject.

While the breath sampling and analysis system discussed herein as an example is designed for use as a THC detection system, it will be understood that similar systems, with appropriate modification, may be used to detect one or more additional or alternative analytes, as noted earlier. For example, the breath sampling and analysis system architecture discussed herein may also be used generally to capture breath samples that may then be analyzed to determine amounts of other controlled substances (or byproducts of using such controlled substances). In general, the systems and architecture provided herein allow for breath samples containing potentially very small volumetric densities or concentrations of analytes, e.g., with magnitudes on the picogram-per-liter scale, to be captured and concentrated in reaction volumes on the order of microliters or tens of microliters within microfluidic circuits/plates. Once captured, such volumes may be analyzed to determine the presence and quantity of a particular analyte of interest, e.g., according to any of the assay techniques discussed earlier. As discussed, while most of the discussion herein is with reference to an example such system for detecting THC, the principles set forth herein, and the overall architecture, may be applicable to systems for detecting a variety of different analytes, and the concepts laid out herein should not be viewed as being solely directed to THC detection systems and methods.

According to various embodiments the present technology provides a simplified design using label-free, direct detection of THC in breath samples (i.e., rather than urine, saliva, or blood samples) using a SERS substrate. Furthermore, SERS produces Raman signals that are orders of magnitude greater than traditional Raman scattering detection ("bulk Raman"), thus, the present technology allows enhanced sensitivity including single molecule sensitivity of THC in breath samples. Moreover, the present technology allows specific detection of THC because the SERS spectrum is a "signature" of the molecule being detected rather than using a label. Additionally, since measurement is done right at the point of collection in various embodiments, the target analyte (e.g., THC) is in its most concentrated form, allowing for maximal use of a collected sample (e.g., breath sample).

Data obtained from any of the devices, apparatuses, systems, and methods herein can be retained within the device in which the measurement has been made. Further, such data may be otherwise stored (e.g., in a memory, a server, a cloud server, etc.), transmitted (e.g., in a wired or wireless manner to a local network or the Internet, etc.), or communicated in any useful manner.

OTHER EMBODIMENTS

This application incorporates by reference the following applications for their disclosure relating to implementation of biomarker (which may be considered an analyte) capture, collection, detection, measurement and analysis methods and apparatus that are suitable for implementation of the disclosed methods and devices: U.S. application Ser. No. 16/425,938, filed May 29, 2019, titled "SINGLE-USE MICROFLUIDIC CARTRIDGE FOR DETECTION OF TARGET CHEMICAL PRESENCE IN HUMAN BREATH" and U.S. application Ser. No. 16/425,943, filed May 29, 2019, titled "MECHANICAL BREATH COLLECTION DEVICE" and International Application No. PCT/US2020/013553, filed Jan. 14, 2020, published as International Publication No. WO 2020/159698, titled "MECHANICAL BREATH COLLECTION DEVICE" and U.S. application Ser. No. 16/776,501, filed Jan. 29, 2020, titled "NONINVASIVE POINT OF CARE BIOMARKER DETECTION FROM BREATH SAMPLES," each of which claims priority to U.S. Provisional Patent Application No. 62/799,675, filed Jan. 31, 2019, titled "NON-INVASIVE POINT OF CARE BIOMARKER DETECTION FROM BREATH SAMPLES"; U.S. application Ser. No. 16/729,116, filed Dec. 27, 2019, titled "ANALYTE DETECTION FROM BREATH SAMPLES," which claims priority to U.S. Provisional Patent Application No. 62/786,222, filed Dec. 28, 2018, titled "ANALYTE DETECTION FROM BREATH SAMPLES"; U.S. application Ser. No. 16/823,113, filed Mar. 18, 2020, titled "BIOMARKER DETECTION FROM BREATH SAMPLES," which claims priority to U.S. Provisional Application No. 62/821,900, filed Mar. 21, 2019, titled "BIOMARKER DETECTION FROM BREATH SAMPLES"; from U.S. application Ser. No. 16/124,181, filed Sep. 6, 2018, titled "ANALYTE DETECTION FROM BREATH SAMPLES," which claims priority to U.S. Provisional Application No. 62/646,798, filed Mar. 22, 2018, titled "ANALYTE DETECTION FROM BREATH SAMPLES"; U.S. application Ser. No. 16/655,182, filed Oct. 19, 2019, titled "ROTARY VALVE ASSEMBLIES AND METHODS OF USE FOR BREATH SAMPLE CARTRIDGE SYSTEMS," which claims priority to U.S. Provisional Application No. 62/746,858, filed Oct. 17, 2018, titled "BREATH SAMPLE CARTRIDGE AND SYSTEM"; and U.S. Provisional Application No. 63/201,389, filed Apr. 27, 20201, titled "BREATH ANALYTE DETECTION AND MEASUREMENT."

This application also incorporates by reference the following applications for their disclosure relating to implementation of biomarker (or analyte) collection and detection methods and apparatus that are suitable for implementation of the disclosed methods and devices: U.S. Provisional Application No. 62/557,056, filed Sep. 11, 2017, titled "IMMUNOASSAY METHODS FOR DETECTING THC IN BREATH"; U.S. Provisional Application No. 62/557,060, filed Sep. 11, 2017, titled "DIAGNOSTIC AND ANALYTICAL ASSAY PERFORMANCE FOR THC IMMUNOASSAY"; U.S. Provisional Application No. 62/616,380, filed Jan. 11, 2018, which is titled "METHOD AND DEVICE FOR MEASURING THC LEVEL FROM BREATH SAMPLE"; U.S. Provisional Patent Application No. 62/337,286, filed May 16, 2016, and titled "BREATH COLLECTOR MODULE"; U.S. Provisional Patent Application No. 62/351,858, filed Jun. 17, 2016, and titled "COMPOSITIONS AND METHODS FOR DETECTION OF TARGET CONSTITUENT IN EXHALED BREATH"; U.S. Provisional Patent Application No. 62/351,821, filed Jun. 17, 2016, and titled "SYSTEM AND METHOD FOR TARGET SUBSTANCE IDENTIFICATION"; U.S. patent application Ser. No. 15/217,151, filed Jul. 22, 2016, and titled "COMPOSITIONS AND METHODS FOR DETECTION OF TARGET CONSTITUENT IN EXHALED BREATH"; U.S. Provisional Patent Application No. 62/351,858, filed Jun. 17, 2016, and U.S. patent application Ser. No. 14/997,405, titled "METHOD, DEVICE AND SYSTEM FOR TARGET SUBSTANCE DETECTION" and filed Jan. 15, 2016, U.S. Provisional Application Nos. 62/104,813, filed Jan. 18, 2015, and 62/107,331, filed Jan. 23, 2015, both of which are titled "METHOD, DEVICE AND SYSTEM FOR TARGET SUBSTANCE DETECTION," U.S. Provisional Application No. 62/277,854, filed Jan. 12, 2016, and titled "PORTABLE, HAND-HELD INSTRUMENT FOR DETECTION AND QUANTIFICATION OF CANNABINOIDS AND ALCOHOL IN EXHALED HUMAN BREATH," and U.S. Provisional Application Nos. 62/508,864, filed May 19, 2017, and 62/514,618, filed Jun. 2, 2017, both of which are titled "SYSTEM AND METHOD FOR TARGET SUBSTANCE IDENTIFICATION."

In the description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, they have been presented by way of example only, and not limitation. The descriptions are not intended to limit the scope of the present technology to the forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A handheld breath sample apparatus for detection of tetrahydrocannabinol (THC) in a breath sample using Surface-Enhanced Raman Spectroscopy (SERS), the apparatus comprising:
   a housing comprising a cartridge interface configured to mechanically interface with a cartridge that has a Surface-Enhanced Raman Spectroscopy (SERS)-active substrate, wherein the SERS-active substrate comprises one or more capture sites for a breath sample; and
   a detection device optically coupled to the SERS-active substrate to detect Raman signals emitted from the SERS-active substrate, and to correlate the Raman signals to a threshold level of THC; and
   wherein the threshold level of THC is correlated with an average amount of THC in breath between 2 and 3 hours after inhalation.

2. The apparatus of claim 1, wherein the SERS-active substrate comprises metal nanoparticles.

3. The apparatus of claim 2, wherein the metal nanoparticles are at least one of gold nanoparticles and silver nanoparticles.

4. The apparatus of claim 3, wherein the THC present in the breath sample is absorbed or adsorbed at or in the capture sites.

5. The apparatus of claim 4, wherein a surface of the SERS-active substrate is configured to cause excitement of localized surface plasmons upon exposure to a laser light, thereby enhancing the Raman signals and allowing for trace detection of THC.

6. The apparatus of claim 5, wherein the enhancing of the Raman signals is $10^3$ to $10^{10}$-fold signal increase, as compared to traditional "bulk" Raman scattering, by a strong electromagnetic wave coupling of the Raman signals.

7. The apparatus of claim 6, wherein the trace detection of THC is single molecule detection of THC in the breath sample.

8. The apparatus of claim 1, wherein the SERS-active substrate is configured to facilitate droplet capture through inertial impaction.

9. The apparatus of claim 8, further comprising:
   an impaction port disposed within the housing, wherein the impaction port has a longitudinal axis that is perpendicular to a major plane of the SERS-active substrate, and wherein the impaction port is configured to be in fluidic communication with the one or more capture sites disposed on a surface of the SERS-active substrate.

10. The apparatus of claim 9, further comprising:
    an interface or a laser source configured to optically access the one or more capture sites.

11. A method using Surface-Enhanced Raman Spectroscopy (SERS) for detection of tetrahydrocannabinol (THC) in a breath sample, the method comprising:
    determining an amount of THC captured from a breath sample using SERS using a SERS-active substrate, wherein the SERS-active substrate comprises one or more capture sites for a breath sample;

comparing the determined amount of THC captured from the breath sample to a threshold level for THC in breath;

indicating whether the determined amount of THC captured from the breath sample exceeds the threshold level; and wherein the threshold level of THC is correlated with an average amount of THC in breath between 2 and 3 hours after inhalation.

12. The method of claim 11, wherein the determining an amount of THC captured from a breath sample using SERS comprises receiving enhanced Raman signals that is $10^3$ to $10^{10}$ fold signal increase, as compared to traditional "bulk" Raman scattering, by a strong electromagnetic wave coupling of the enhanced Raman signals.

13. The method of claim 11, wherein the SERS-active substrate comprises metal nanoparticles.

14. The method of claim 13, wherein the metal nanoparticle are at least one of gold nanoparticles and silver nanoparticles.

15. The method of claim 11, wherein the threshold is correlated with a baseline maximum level of THC in breath associated with consumption of THC outside a window of THC-associated impairment.

16. The method of claim 11, wherein the determining the amount of THC captured from the breath sample using SERS allows for single THC molecule sensitivity.

17. The method of claim 11, further comprising:

wirelessly transmitting data corresponding to the determining an amount of THC captured from the breath sample using SERS, the comparing the determined amount of THC from the breath sample to the threshold level for THC in breath, and the indicating whether or not the determined amount of THC captured from the breath sample exceeds the threshold, to a remote location.

18. The method of claim 11, wherein the THC captured from the breath sample using SERS is captured with a hand-held device.

19. A system using Surface-Enhanced Raman Spectroscopy (SERS) for detection of tetrahydrocannabinol (THC) in a breath sample, the system comprising:

an excitation laser configured to excite a SERS-active substrate, wherein the SERS-active substrate comprises one or more capture sites for the breath sample;

a high sensitivity spectrometer configured to collect one or more Raman signals from the one or more capture sites;

a detector electrically connected to the high sensitivity spectrometer; and wherein the one or more Raman signals are directly proportional to a threshold level of THC captured in the breath sample, wherein the threshold level of THC is correlated with an average amount of THC in breath between 2 and 3 hours after inhalation.

20. The system of claim 19, wherein the SERS-active substrate comprises gold nanoparticles, silver nanoparticles, and/or copper nanoparticles.

21. The system of claim 19, further comprising:

a cartridge, the cartridge comprising the SERS-active substrate including the one or more capture sites for the breath sample.

* * * * *